United States Patent

Hiruma et al.

(10) Patent No.: US 7,176,217 B2
(45) Date of Patent: Feb. 13, 2007

(54) AZABICYCLO COMPOUND MATRIX METALLOPROTEASE INHIBITOR AND SKIN PREPARATION

(75) Inventors: Takuya Hiruma, Yokohama (JP); Koji Kobayashi, Yokohama (JP); Shinji Inomata, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 239 days.

(21) Appl. No.: 10/495,370

(22) PCT Filed: Nov. 13, 2002

(86) PCT No.: PCT/JP02/11816

§ 371 (c)(1),
(2), (4) Date: May 11, 2004

(87) PCT Pub. No.: WO03/042176

PCT Pub. Date: May 22, 2003

(65) Prior Publication Data

US 2005/0009808 A1    Jan. 13, 2005

(30) Foreign Application Priority Data

Nov. 13, 2001    (JP)    ............. 2001-347554

(51) Int. Cl.
*A61K 31/44*    (2006.01)
(52) U.S. Cl. .................... 514/304; 514/412; 546/135; 548/453
(58) Field of Classification Search ................ 514/304, 514/412; 546/135; 548/453
See application file for complete search history.

(56) References Cited

FOREIGN PATENT DOCUMENTS

EP    0 895 988 A1    2/1999
WO    WO 98/08815 A1    3/1998
WO    WO 99/65867    12/1999

OTHER PUBLICATIONS

Kaori Miyazaki et al., "Biochemistry", vol. 68, No. 12, pp. 1791-1807 (1996).
Gary J. Fisher et al., "Nature", vol. 379, No. 25, pp. 335-339 (1996).
Gary J. Fisher et al., "Pathophysiology of Premature Skin Aging Induced By Ultraviolet Light", The New England Journal of Medicine, vol. 337, No. 20, pp. 1419-1428. (1997).

*Primary Examiner*—Amelia A. Owens
(74) *Attorney, Agent, or Firm*—Fei-Fei Chao; Andrews Kurth LLP

(57) ABSTRACT

An azabicyclo compound (I) or a salt thereof in accordance with the present invention has an excellent inhibiting action on matrix metalloproteases (MMPs) activity, and is useful for pharmaceutical, cosmetic and skin external compositions.

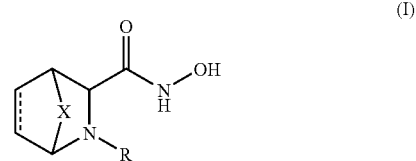

wherein R is H, alkyl, heteroalkyl, aryl, heteroaryl, arylalkyl, heteroarylalkyl, acyl, $COOR^1$, carbamoyl or $SO_2R^2$ (wherein $R^1$ and $R^2$ each are alkyl, heteroalkyl, aryl, heteroaryl, arylalkyl or heteroarylalkyl); X is methylene, ethylene or propylene; and

----- is a single bond or a double bond.

12 Claims, No Drawings

AZABICYCLO COMPOUND MATRIX METALLOPROTEASE INHIBITOR AND SKIN PREPARATION

RELATED APPLICATIONS

This application claims priority to Japanese Patent Application No. 2001-347554 filed on Nov. 13, 2001, which is incorporated herein by reference.

FIELD OF THE INVENTION

The present invention relates to an azabicyclo compound and, in particular, to a matrix metalloproteases (MMPs) inhibitor.

BACKGROUND OF THE INVENTION

A human skin is roughly classified into three layers of epidermis, dermis and subcutaneous tissue, and epidermis and dermis are contacted each other through a basement membrane.

An epidermic cell contacting with the basement membrane repeats division without cease, and the divided epidermic cells are successively pushed upward to form stratum corneum, which is the uppermost layer of epidermis, via differentiation. Stratum corneum is an extremely important site from a viewpoint of beauty. Since the basement membrane structure has great influence on division of epidermic cells, it can be said that the basement membrane also has great influence on a skin.

The basement membrane is one of extracellular matrices, and is composed of type IV collagen, proteoglycan, laminin, fibronectin and the like.

An extracellular space in dermis is filled mainly with a network structure of a huge macromolecule called extracellular matrix (ECM). The ECM is composed of fibrous proteins such as collagen, elastin, fibronectin, laminin and the like, and polysaccharides called glycosaminoglycan or proteoglycan. Due to such the structure, dermis has great influence on elasticity and tension of a skin.

Up to now, it has been known that ultraviolet ray is greatly involved in changes of a skin accompanied with aging, that are, wrinkles, dullness, lost of texture, reduction in elasticity and the like. When these changes are observed microscopically, in dermis, ECM components such as collagen, elastin and the like are reduced and denatured and, further, damage of a basement membrane and thickening of epidermis occur.

With progress of recent study, as a factor inducing these changes, in particular, involvement of matrix metalloproteases (MMPs) is pointed out. MMPs is a generic name of a group of metalloproteases which main substrate is an extracellular matrix protein. Many kinds of MMPs are known, and they have common structural or functional characteristics, but their substrate proteins are different from each other (Kaori Miyazaki et al. "Biochemistry", vol. 68, No. 12, pp. 1791–1807 (1996)).

MMPs are usually classified into collagenase group, gelatinase group, stromlycin group, and others (matrilycin etc.) in view of their structures and functions.

The collagenase group includes MMP-1 (interstitial collagenase), MMP-8, MMP-13 and the like. Inter alia, MMP-1 is known to be an enzyme degrading type I collagen, type III collagen and the like, which are main components of dermis matrix. Also, MMP-8 and MMP-13 have the action of degrading type I collagen and the like.

The gelatinase group includes MMP-2, MMP-9 and the like. MMP-2 and MMP-9 are known to be an enzyme degrading type IV collagen and laminin which are basement membrane components, and degrading elastin and the like which are dermis matrix components.

The stromlycin group includes MMP-3, MMP-10 and the like. MMP-3 and MMP-10 are known to be an enzyme degrading proteoglycan, type IV collagen, laminin and the like.

Also, expressions of these respective enzymes are greatly increased by irradiation of ultraviolet ray, which becomes one cause of reduction and denaturation in ECM by ultraviolet ray. This is thought to be one great factor for wrinkle-formation and the like on a skin (Gary J. Fisher et al., "Nature", 379 (25), 335(1996); Gary J. Fisher et al, "The New England Journal of Medicine", 337(20), 1419(1997)).

Therefore, it is considered that inhibition of MMPs activity is important in protecting the basement membrane and various extracellular matrices, and improving or preventing skin aging such as wrinkles and slacks. Thus, excellent MMPs inhibiting substances are desired.

In addition, since MMPs are involved in tissue matrix degradation as described above, it is suggested that MMPs are involved in many disease states accompanying abnormal metabolism of a connecting tissue or a basement membrane matrix, for example, arthritis (rheumatoid arthritis, osteoarthritis etc.), bone disease (osteoporosis etc.), periodontal disease, ectopic angiogenesis, multiple sclerosis, metastasis of tumor, and tissue ulcer formation (ulcer formation of cornea, epidermis, stomach etc.) (WO 98/08815 etc.). Therefore, MMPs inhibitor is also expected as an agent for treating or preventing these diseases due to abnormal metabolism of tissue matrix.

SUMMARY OF THE INVENTION

An object of the present invention is to provide a compound having the MMPs inhibiting action, and to provide a MMPs inhibitor, a pharmaceutical composition, a cosmetic composition and a skin external composition containing the same as an active ingredient.

In order to solve the aforementioned problems, the present inventors intensively studied and, as a result, found that a particular azabicyclo compound has an excellent MMPs inhibiting action, which resulted in completion of the present invention.

That is, the azabicyclo compound of the present invention is represented by the following formula (I):

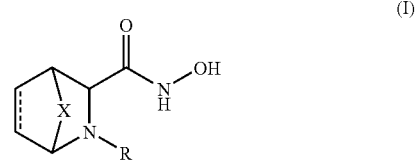

wherein R is hydrogen atom, alkyl, heteroalkyl, aryl, heteroaryl, arylalkyl, heteroarylalkyl, acyl, COOR$^1$, carbamoyl or SO$_2$R$^2$;

R$^1$ and R$^2$ each are alkyl, heteroalkyl, aryl, heteroaryl, arylalkyl or heteroarylalkyl;

X is methylene, ethylene or propylene; and

----- is a single bond or a double bond.

In the present invention, R is preferably $SO_2R^2$, and $R^2$ is preferably aryl.

Also, in the present invention, X is preferably methylene.

A matrix metalloprotease inhibitor of the present invention comprises, as an active ingredient, said azabicyclo compound or the pharmacologically acceptable salt thereof.

A cosmetic composition of the present invention comprises, as an active ingredient, said azabicyclo compound or the pharmacologically acceptable salt thereof.

A pharmaceutical composition of the present invention comprises, as an active ingredient, said azabicyclo compound or the pharmacologically acceptable salt thereof.

A skin external composition of the present invention comprises, as an active ingredient, said azabicyclo compound or the pharmacologically acceptable salt thereof.

DESCRIPTION OF THE PREFERRED EMBODIMENT

In the present invention, R can be hydrogen atom, alkyl, heteroalkyl, aryl, heteroaryl, arylalkyl, heteroarylalkyl, acyl, $COOR^1$, carbamoyl or $SO_2R^2$, wherein $R^1$ and $R^2$ each can be alkyl, heteroalkyl, aryl, heteroaryl, arylalkyl or heteroarylalkyl. Preferable R is $SO_2R^2$.

Preferable $R^2$ of $SO_2R^2$ can be aryl including phenyl and biphenylyl, preferably, phenyl. Also, the aryl may be substituted by a substituent such as alkyl, alkoxy, aryloxy, heteroaryloxy, halogen atom, amino or acylamino group, preferably alkoxy or halogen atom.

In the present invention, X is methylene, ethylene or propylene, preferably methylene.

In the formula (I),

----- is a single bond or a double bond, preferably a single bond.

Each substituent of the present invention, unless there are any problems, may be substituted with one or more substituents at a feasible position. Such substituents include alkyl, alkenyl, alkynyl, alkoxy, alkylamino, heteroalkyl, aryl, arylalkyl, aryloxy, arylamino, heteroaryl, heteroarylalkyl, heteroaryloxy, heteroarylamino, acyl, hydroxy, oxo, thioxo, carboxyl, alkoxycarbonyl, halogen atom, amino, nitro, mercapto, alkylthio and cyano groups, which can be combined.

When $R^2$ is alkyl, the alkyl may be substituted with $-Z^1-A^1$, wherein $Z^1$ is C≡C, CONH, NHCO, O or S; and $A^1$ is heteroalkyl, aryl or heteroaryl.

When $R^2$ is aryl, the aryl may be substituted with $-Z^2-A^2$, wherein $Z^2$ is C≡C, CONH, NHCO, O or S; and $A^2$ is alkyl, heteroalkyl, aryl or heteroaryl.

Unless otherwise indicated, definition of each group is as follows.

The alkyl, which may be straight or branched, is preferably a saturated hydrocarbon group having 1–6 carbon atoms such as methyl, ethyl, n-propyl, isopropyl, n-butyl, isobutyl, sec-butyl, tert-butyl, n-pentyl, isoamyl and n-hexyl. Also, cyclic alkyl groups such as cyclopropyl, cyclobutyl, cyclopentyl and cyclohexyl are included therein.

The heteroalkyl, which may be straight or branched, is a saturated group consisting of a carbon atom and one or more heteroatoms, preferably a group having 2–6 atoms. Also, cyclic heteroalkyl groups such as piperidinyl, piperaziny, morpholyl, thiomorpholyl and tetrahydrofuryl are included therein.

The aryl is a aromatic carbon ring group. Preferable examples of the aryl group include phenyl, tolyl, biphenyl and naphthyl groups.

The arylalkyl is an alkyl group substituted with a aryl group. Preferably examples thereof include benzyl and phenylethyl.

The heteroaryl is an aromatic heterocyclic group. Preferable examples of the heteroaryl group include thienyl, furyl, pyrrolyl, pyridinyl, pyrazinyl, thiazolyl, pyrimidinyl, quinolinyl, tetrazolyl, benzothiazolyl, benzofuryl and indolyl.

The heteroarylalkyl group is an alkyl group substituted with a heteroaryl group.

The halogen atom is chlorine, bromine, fluorine or iodine atom.

The heteroatom is nitrogen, oxygen, or sulfur atom. When a group has 2 or more heteroatoms, the heteroatoms may be different form each other.

The acyl is a carbonyl group having hydrogen atom, alkyl, heteroalkyl, aryl, heteroaryl, alkenyl or alkynyl. Examples thereof include acetyl, prop ionyl, butyryl, acryloyl and benzoyl. The acyl of R is preferably a carbonyl group having alkyl, heteroalkyl, aryl or heteroaryl.

The carbamoyl (—$CONH_2$) can be unsubstituted or substituted carbamoyl. The substituted carbamoyl includes a carbamoyl having one or two substituents selected from the group of alkyl, heteroalkyl, aryl, heteroaryl, arylalkyl and heteroarylalkyl. Also, the nitrogen atom in the carbamoyl group may be a member of a hetero ring having 5–6 members. This 5- or 6-memberd hetero ring may contain one or two additional heteroatoms selected from N, O and S. Furthermore, the hetero ring may have at least one substituent selected from the group of alkyl, heteroalkyl, aryl, heteroaryl, arylalkyl, heteroarylalkyl, oxo, halogen atom, hydroxy and alkoxy groups at a feasible position.

The mercapto can be an unsubstituted or substituted mercapto with a substituent such as alkyl, heteroalkyl, aryl or heteroaryl.

The alkenyl, which may be straight or branched, is preferably an unsaturated hydrocarbon group having 2–6 carbon atoms and having at least one double bond at any position. Also, a cyclic alkenyl group such as cyclopentenyl, cyclobutenyl, cyclopentenyl or cyclohexenyl group is included herein.

The alkynyl is preferably an unsaturated hydrocarbon group having 2–6 carbon atoms and at least one triple bond at any position.

The alkoxy is an oxy group having an alkyl group.

The alkylamino is an amino group having one or two alkyl groups.

The acylamino is an amino group having one or two acyl groups.

The aryloxy is an oxy group having an aryl group.

The arylamino is an amino group having one or two aryl groups.

The heteroaryloxy is an oxy group having a heteroaryl group.

The heteroarylamino is an amino group having one or two heteroaryl groups.

The alkoxycarbonyl is a carbonyl group having an alkoxy group.

The alkylthio is a thio group having an alkyl group.

The azabicyclo compound (I) of the present invention may have one or more asymmetric centers therein. The present compound may be an enantiomer, a diastereomer or a mixture thereof based on the asymmetric carbon. In the present invention, the following azabicyclo compound (II) wherein the carbon atom at 3-position substituted with a group of —CO—NH—OH has R-configuration is preferable.

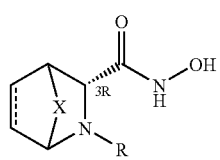

(II)

In addition, when there are other isomers such as a conformational isomer and a geometrical isomer, these can be also included in the present invention.

Hereinafter, a representative process for preparing the present compound (I) is exemplified, and the present invention is not limited thereto. In the following process, unless explicitly indicated, R and X are as defined above. In order to obtain the compound as an optically active substance, an optically active material, reagent, catalyst or the like may be used. Also, at a suitable step, a separating operation such as chromatography or fractional crystallization may be performed. Further, when there are a conformational isomer and a geometrical isomer, a starting material and a reaction condition can be selected suitably and then separating operation can be performed to obtain a pure conformational isomer or a geometrical isomer.

Furthermore, when there is a functional group in the molecule and said functional group becomes or in danger of a disturbance of reaction, it is preferable that a suitable protecting group is used to put the reaction forward effectively. Use of protecting group can be performed, for example, according to Protective Groups in Organic Synthesis by Theodora W. Greene, Peter G. M. Wuts et al. Also, unless there is any problem, a reaction condition and order of process can be changed, thereby selecting more suitable method.

Scheme 1

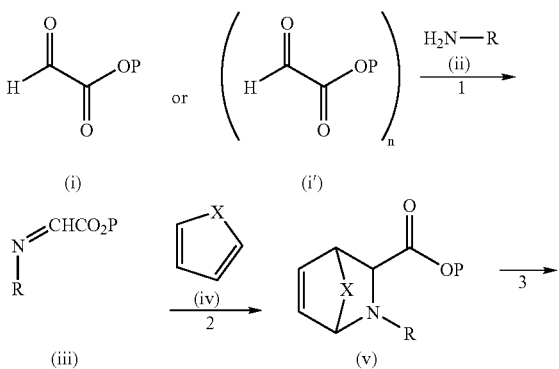

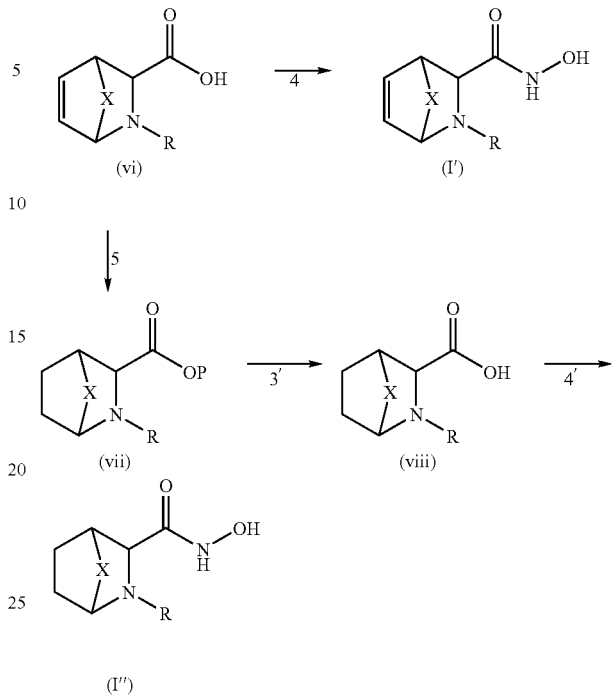

According to Reactions 1–4 of Scheme 1, Compound (I') of the present invention, which has a double bond in azabicyclo ring can be obtained.

In Reaction 1, for example, in a solvent such as dichloromethane or toluene, glyoxylate (i) or its polymer form (i') (wherein P represents a protecting group such as alkyl) is reacted with an amine (ii) to prepare an imine (iii).

In Reaction 2, by Diels-Alder reaction using said imine (iii) and a diene (iv), an azabicyclo ring is formed to obtain a compound (v). This reaction can be performed, for example, in a solvent such as N,N-dimethylformamide in the presence of an acid (e.g., trifluoroacetic acid, boron trifluoride diethyl etherate, etc.).

In Reaction 3, using a standard method for hydrolyzing an ester, a carboxylic acid (vi) can be obtained from the compound (v).

In Reaction 4, the carboxylic acid (vi) or its corresponding activated compound is reacted with hydroxylamine or its acid-added salt (e.g., hydrochloride), to obtain a compound (I') of the present invention. This reaction can be performed, for example, in the presence of a base (e.g., triethylamine) in a solvent such as dimethylformamide, tetrahydrofuran or dichloromethane.

The activated compound corresponding to the carboxylic acid represents, for example, an acid anhydride (in particular, a mixed acid anhydride), an acid halide or an activated ester. The mixed acid anhydride can be prepared, for example, by using pivaloyl chloride or ethyl chlorocarbonate. The acid halide is preferably acid chloride and can be prepared, for example, by using thionyl chloride or oxalyl chloride. The activated ester can be prepared, for example, in the presence or absence of 1-hydroxybenzotriazol using 1,1'-carbonyldiimidazole, N-(dimethylaminopropyl)-N'-ethylcarbodiimide or dicyclohexyl carbodiimide.

On the other hand, when a compound (I") of the present invention having a saturated azabicyclo ring is obtained, at a suitable step in the synthesis of said compound (I') the double bond may be reduced. For example, the compound (v) obtained in said Reaction 2 may be reduced.

That is, in Reaction 5, the double bond can be reduced by hydrogenation to obtain a compound (vii) from the compound (v). The hydrogenation includes, for example, a reaction under a hydrogen atmosphere in a solvent such as ethanol or ethyl acetate using a metallic catalyst such as Pd—C.

The compound (vii) can be subjected to Reaction 3' and Reaction 4' according to said Reaction 3 and Reaction 4 respectively to obtain a compound (I") of the present invention.

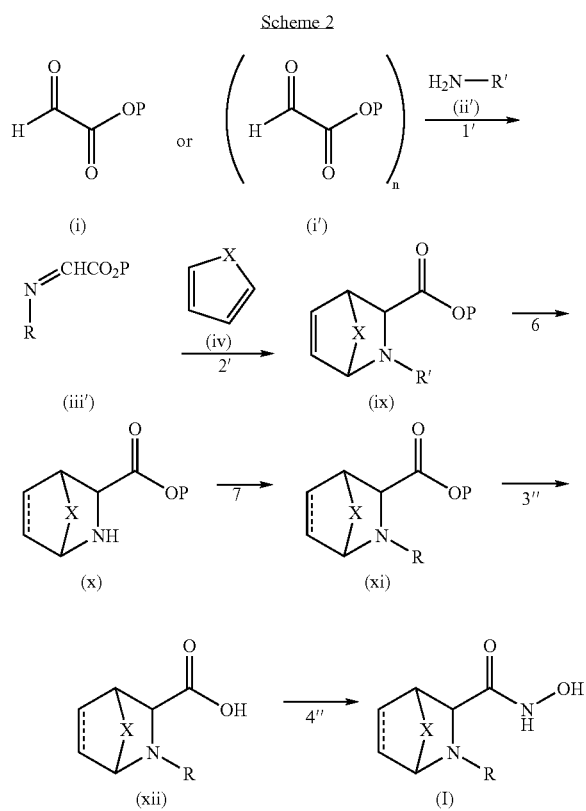

Scheme 2

Also, in place of the amine (ii) of Scheme 1, an amine (ii') having a group of R' (R' is an amine-protecting group such as benzyl group) can be used.

That is, as shown in Reaction 1' of Scheme 2, first, an imine (iii') is obtained form glyoxylate (i) or its polymer form (i') and an amine (ii'). This reaction may be performed according to said Reaction 1.

In Reaction 2', a Diels-Alder reaction between the imine (iii') and the diene (iv) according to said Reaction 2 can be performed to obtain a compound (ix).

In Reaction 6, the protecting group R' of the compound (ix) is removed and, if necessary, the double bond is reduced to a single bond, to obtain a compound (x). For example, when R' is t-butoxycarbonyl group, it can be removed with trifluoroacetic acid or the like. The reduction of the double bond to a single bond may be performed, for example, under a hydrogen atmosphere in a solvent such as ethanol or ethyl acetate using a metallic catalyst such as Pd—C. When R' is benzyl group or the like, the removal of the protecting group R' and the reduction of the double bond to a single bond can be performed at the same time, for example, by a reaction in a solvent such as ethanol or ethyl acetate using a metallic catalyst such as $Pd(OH)_2$.

In Reaction 7, a substituent R is introduced into the compound (x) to obtain a compound (xi). For example, in a solvent such as chloroform in the presence of a base (e.g., triethylamine), a reaction with halide R—X' (X' is a halogen such as chlorine or bromine) may be performed. Alternatively, a similar reaction using R"—X (R" is a group that can be converted to R) in place of R—X' can be performed and then R" can be converted into R at a suitable step.

The compound (xi) can be subjected to Reaction 3" and Reaction 4" according to said Reaction 3 and Reaction 4 respectively, to obtain the compound (I) of the present invention.

In addition, when reactions according to said Reactions 3, 4 and 6 are appropriately combined and the compound (ix) is subjected thereto, a compound of the present invention wherein R=H can be synthesized.

The diene (iv) can be commercially available or synthesized by a known method. For example, cyclopentadiene can be obtained by thermolysis of its dimer, dicyclopentadiene. Other starting materials and reagents can be commercially available or synthesized by appropriately combined known methods.

The azabicyclo compound (I) of the present invention can be converted into an acid-added salt by a conventional method, if necessary. Examples of an acid of the acid-added salt include inorganic acids such as hydrochloric acid, hydrobromic acid, sulfuric acid and phosphoric acid, and organic acids such as acetic acid, propionic acid, citric acid, lactic acid, oxalic acid, maleic acid, fumaric acid, succinic acid, tartaric acid and methanesulfonic acid. These salts are also included in the present invention.

Since the azabicyclo compound (I) of the present invention has an excellent MMPs inhibiting action, it is useful as an agent for treating or preventing diseases which can be expected to be improved by the present action, for example, rheumatoid arthritis, osteoarthritis, osteoporosis, periodontal disease, ectopic angiogenesis, multiple sclerosis, metastasis of tumor, cornea ulcer and the like.

When the azabicyclo compound (I) of the present invention is administered for the medical purpose, an administration route is not particularly limited, and the compound can be administered by any method, for example, orally, parenterally or locally. A dose is appropriately adjusted depending on subject (mammal, particularly human), an age, sex, individual difference, symptom and the like, being not particularly limited. For example, a dose of 0.1 to 500 mg/kg, preferably 0.5 to 200 mg/kg of the azabicyclo compound (I) of the present invention can be administered orally or parenterally in a single dose or several doses per day.

The azabicyclo compound (I) of the present invention can be administered in various preparation forms. An amount of an active ingredient in a preparation is not particularly limited, but is usually 0.01% to 70% by weight, preferably 0.1 to 50% by weight.

A preparation is prepared using a normal preparation carrier by a conventional method and, if necessary, pharmacologically acceptable additives may be added thereto.

That is, when an oral solid preparation is prepared, an excipient and, further, if necessary, a binder, a disintegrating agent, a lubricant, a colorant, a corrigent and the like are added to an active component to form tablets, coated tablets, granules, powders, capsules or the like by a conventional method.

As the excipient, for example, lactose, corn starch, sucrose, glucose, sorbit, crystalline cellulose, silicon dioxide, calcium phosphate, glycine and the like can be used. As the binder, for example, polyvinyl alcohol, polyvinyl ether, ethyl cellulose, methyl cellulose, gum arabic, tragacanth, gelatin, shellac, hydroxypropyl cellulose, hydroxypropyl starch, polyvinylpyrrolidone and the like can be used. As the disintegrating agent, for example, starch, agar, gelatin powder, crystalline cellulose, calcium carbonate, sodium hydrogencarbonate, calcium citrate, sodium citrate, dextrin, pectin, alginic acid and the like can be used. As the lubricant, for example, magnesium stearate, sodium laurate, talc, polyethylene glycol, silica, hydrogenated vegetable oil and the like can be used. As the colorants, those are permitted to be added to pharmaceutical preparations can be used. As the corrigent, cocoa powder, menthol, aromatic acid, mentha oil, borneol and cinnamon powder can be used. If necessary, tablets, granules and the like can be appropriately coated with a sugar coating, a gelatin coating or the like.

When an oral liquid formulation is prepared, a corrigent, a colorant, an emulsifying agent, a suspending agent, a diluent and the like may be added to an active ingredient to form an aqueous suspension, an elixir, a syrup or the like.

An injection (intramuscular, intraperitoneal, intra-articular, subcutaneous, intraveneous injections or the like) can be a sterile aqueous or non-aqueous solution, suspension and emulsion. If necessary, auxiliary agents such as an antiseptic, a wetting agent, an emulsifying agent, a dispersing agent, a stabilizer and a solubilizer may be contained therein. An injection is usually sterilized by filtration (bacteria—retaining filter etc.), incorporation of a germicide or γ-ray irradiation. Alternatively, after these treatments, it is converted into a solid composition by freeze-drying or the like, which is used by adding sterile water or sterile injectable diluent thereinto just before use.

The compound may be also administered parenterally as a suppository.

Further, the azabicyclo compound (I) of the present invention may be incorporated into a skin external composition, which is particularly effective as an anti-aging cosmetic for the purpose of improving or preventing skin aging such as wrinkles, slacks and dullness of a skin. The "anti-aging cosmetic" in the present invention broadly means a cosmetic for preventing or improving aging, in particular, aging of a skin.

When the present compound is used in a skin external composition, an amount of the azabicyclo compound (I) to be incorporated is 0.00001 to 10% by weight, preferably 0.0001 to 5% by weight in a total amount of the composition. When the amount is less than 0.00001% by weight, the effect is not sufficiently exerted. On the other hand, when the amount exceeds 10% by weight, considerable improvement in the effect is not recognized, and formulation becomes difficult in some cases.

Into the skin external composition of the present invention, if necessary, can be appropriately incorporated other ingredients which are usually used in an external composition such as a cosmetic or pharmaceutical product in addition to the azabicyclo compound (I) as an active ingredient, within a range that the effect of the present invention is not deteriorated. For example, a whitening agent, a humectant, an antioxidant, an oily ingredient, an ultraviolet absorbing agent, a surfactant, a thickener, an alcohol, a powder ingredient, a coloring agent, an aqueous ingredient, water, various skin nutrients and the like can be incorporated therein.

Further, a metal sequestering agent such as disodium edatate, trisodium edatate, sodium citrate, sodium polyphosphate, sodium metaphosphate, or gluconic acid; a drug such as caffeine, tannin, verapamil, tranexamic acid and a derivative thereof, a glycyrrhiza extract, glove lysine, hot water extract of a fruit of Chinese quince, various crude drugs, tocopherol acetate, or glycyrrhizic acid and a derivative thereof and a salt thereof; a whitening agent such as vitamin C, magnesium ascorbylphosphate, ascorbyl glucoside, arbutin or kojic acid; a sugar such as glucose, fructose, mannose, sucrose or trehalose; a vitamin A derivative such as retinoic acid, retinol, retinol acetate or retinol palmitate; and the like may be appropriately incorporated therein.

The form of the skin external composition is not particularly limited, and can be arbitrary forms such as solution system, solubilized system, emulsified system, powder dispersed system, water-oil biphase system, water-oil-powder triphase system, solid, ointment, gel, aerosol, mousse and the like. In addition, its use form is also arbitrary, and may be a base cosmetic such as a lotion, an emulsion, a cream, a pack, an essence or the like, a makeup cosmetic such as foundation or the like, a hair cosmetic, a fragrance cosmetic, a bath preparation or the like, but it is not limited thereto.

EXAMPLE

The present invention will be explained by way of embodiments below.

MMPs Inhibition Test (a) Preparation of Sample Solution

A test material was dissolved in dimethyl sulfoxide (DMSO) to the concentration of 10 mM, to prepare a stock solution. The stock solution was diluted with a measuring buffer (0.05M tris at pH 7.5 containing 0.2M NaCl and 5 mM $CaCl_2$) to adjust the concentration to 100 μM, which was used as a sample solution. As a control solution, a solution containing no test material was similarly prepared.

(b) Gelatinase Group MMPs Inhibition Test

As a gelatinase group enzyme, MMP-9 (crude enzyme solution derived from a mouse skin) was used. The test was performed according to a gelatin zymography method ("Bio-antioxidant provitamin C", Nobuhiko Miwa ed., p. 76, 1999, Fragrance Journal, Tokyo).

That is, a gel containing gelatin in which a predetermined amount of the crude enzyme solution had been subjected to electrophoresis in advance, was incubated overnight with a sample solution or a control solution. After the gel was stained, the appearing band corresponding to MMP-9 was evaluated by a decrease when its size compared with that of a band of control solution. Evaluation criteria was as follows:

◎: The band disappeared.
○: The band was slightly confirmed.
Δ: The band became narrower than control.
X: Unchanged.

(c) Result

Using the following azabicyclo compounds as a test material, the test was performed. As clearly from Table 1, azabicyclo compounds of the present invention inhibited MMPs activity.

Compound 1:
N-Hydroxy-2-[(4-methoxyphenyl)sulfonyl]-2-azabicyclo [2.2.1]heptane-3-carboxamide Compound 3:
(1S, 3R, 4R)—N-Hydroxy-2-[(4-methoxyphenyl)sulfonyl]-2-azabicyclo[2.2.1]heptane-3-carboxamide Compound 7:
(3R)—N-Hydroxy-2-[(4-methoxyphenyl)sulfonyl]-2-azabicyclo[2.2.2]octane-3-carboxamide Compound 8:
(1S, 3R, 4R)—N-Hydroxy-2-(phenylsulfonyl)-2-azabicyclo[2.2.1]heptane-3-carboxamide Compound 9:
(1S, 3R, 4R)-2-[(4-Chlorophenyl)sulfonyl]-N-hydroxy-2-azabicyclo[2.2.1]heptane-3-carboxamide Compound 12:
(1S, 3R, 4R)-2-[4-(Butoxyphenyl)sulfonyl]-N-hydroxy-2-azabicyclo[2.2.1]heptane-3-carboxamide Compound 13:
(1S, 3R, 4R)-2-[(4-Fluorophenyl)sulfonyl]-N-hydroxy-2-azabicyclo[2.2.1]heptane-3-carboxamide Compound 14:
5-(tert-Butyl)-(1R, 3R, 4S)—N-hydroxy-2-[(4-methoxyphenyl)sulfonyl]-2-azabicyclo[2.2.1]heptane-3-carboxamide

TABLE 1

| Test material | MMPs Inhibition |
| --- | --- |
| Compound 1 | ○~◉ |
| Compound 3 | ○~◉ |
| Compound 7 | ○~◉ |
| Compound 8 | ○ |
| Compound 9 | ○ |
| Compound 12 | ◉ |
| Compound 13 | ○ |
| Compound 14 | ○ |

Example 1

N-Hydroxy-2-[(4-methoxyphenyl)sulfonyl]-2-azabicyclo[2.2.1]heptane-3-carboxamide (Compound 1)

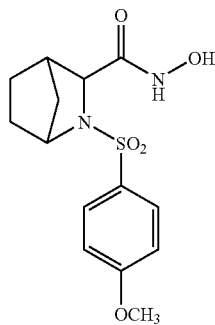

(a) To a solution of ethyl glyoxylate polymer form (45–50% in toluene, 4.68 g) in chloroform (41 ml) were added 3A molecular sieves (4.13 g) and DL-1-phenylethylamine (2.66 ml, 20.6 mmol), and the mixture was stirred under an argon atmosphere at room temperature for 1 hour. 3A molecular sieves were removed by filtration, and then the solvent was evaporated.

To the residue dissolved in N,N-dimethylformamide (15 ml) were successively added trifluoroacetic acid (1.59 ml, 20.6 mmol), boron trifluoride diethyl etherate (2.62 ml, 20.6 mmol) and cyclopentadiene (4.63 ml, 41.3 mmol) at 5-minute intervals under an argon atmosphere at −78° C. After being stirred at −78° C. for 2 hours, the reaction mixture was concentrated. The residue, with saturated sodium bicarbonate water added thereto, was extracted with chloroform. The organic layer was washed with saturated brine and dried over magnesium sulfate. The solvent was evaporated and the residue was purified by silica gel column chromatography (5% ethyl acetate/hexane), to give ethyl 2-(1-phenylethyl)-2-azabicyclo[2.2.1]hept-5-ene-3-carboxylate (4.04 g, 72%).

$^1$H NMR (CDCl$_3$) δ 7.33–7.16 (m, 5H), 6.41 (m, 1H), 6.27 (dd, 1H), 4.30 (s, 1H), 3.81 (m, 2H), 3.03 (q, 1H), 2.90 (brs, 1H), 2.20 (s, 1H), 2.12 (d, 1H), 1.41(d, 4H), 0.95 (t, 3H).

(b) To a solution of ethyl 2-(1-phenylethyl)-2-azabicyclo[2.2.1]hept-5-ene-3-carboxylate (1.29 g, 4.77 mmol) in ethyl acetate (10 ml) was added 20 wt % Pd(OH)$_2$ (1.47 g), and the mixture was stirred under a hydrogen atmosphere at 45° C. for 24 hours. After a filtration through Celite, the solvent was evaporated. The residue was purified by silica gel column chromatography (1%–3% methanol/chloroform), to give ethyl 2-azabicyclo[2.2.1]heptane-3-carboxylate (0.181 g, 22%).

$^1$H NMR (CDCl$_3$) δ 4.18 (q, 2H), 3.53 (s, 1H), 3.31 (s, 1H), 2.62 (s, 1H), 1.68–1.39 (m, 5H), 1.28 (t, 3H), 1.24 (d, 1H).

(c) To a solution of ethyl 2-azabicyclo[2.2.1]heptane-3-carboxylate (664 mg, 3.92 mmol) in chloroform (8 ml) were added triethylamine (0.55 ml, 3.92 mmol) and 4-methoxybenzene sulfonyl chloride (892 mg, 4.32 mmol) while being cooled with ice. After a reaction at room temperature for 4 hours, the reaction mixture was washed with 1N hydrochloric acid, saturated sodium bicarbonate water and saturated brine successively, and dried over magnesium sulfate. The solvent was evaporated and the residue was recrystallized (hexane/ethyl acetate), to give ethyl 2-[(4-methoxyphenyl)sulfonyl]-2-azabicyclo[2.2.1]heptane-3-carboxylate (927 mg, 70%).

$^1$H NMR (CDCl$_3$) δ 7.89 (d, 2H), 6.95 (d, 2H), 4.12–4.06 (m, 3H), 3.93 (s, 1H), 3.86 (s, 3H), 2.70 (d, 1H), 2.04–1.97 (m, 2H), 1.77–1.69 (m, 1H), 1.56–1.44 (m, 2H), 1.31 (d, 1H), 1.22 (t, 3H).

(d) To a solution of ethyl 2-[(4-methoxyphenyl)sulfonyl]-2-azabicyclo[2.2.1]heptane-3-carboxylate (903 mg, 2.66 mmol) in tetrahydrofuran (25 ml) was added 1N sodium hydroxide (15 ml) and the mixture was stirred at room temperature for 3 hours. The reaction mixture was acidified with 1N hydrochloric acid and extracted with ethyl acetate. The organic layer was washed with saturated brine and dried over magnesium sulfate. The solvent was removed, to give 2-[(4-methoxyphenyl)sulfonyl]-2-azabicyclo[2.2.1]heptane-3-carboxylic acid.

$^1$H NMR (CDCl$_3$) δ 7.87 (d, 2H), 6.98 (d, 2H), 4.12 (s, 1H), 3.92 (s, 1H), 3.88 (s, 3H), 2.85 (d, 1H), 1.98–1.87 (m, 2H), 1.77–1.69 (m, 1H), 1.54–1.43 (m, 1H), 1.40–1.34 (m, 2H).

(e) To a solution of 2-[(4-methoxyphenyl)sulfonyl]-2-azabicyclo[2.2.1]heptane-3-carboxylic acid (495 mg, 1.59 mmol) in dichloromethane (6.1 ml) were added oxalyl chloride (0.29 ml, 3.34 mmol) and N,N-dimethylformamide (0.12 ml, 1.59 mmol) while being cooled with ice, and the mixture was stirred at room temperature for 30 minutes. Separately, to a suspension of hydroxylamine hydrochloride (442 mg, 6.36 mmol) in tetrahydrofuran (2.0 ml)-water (0.4 ml) was added triethylamine (1.35 ml, 9.70 mmol) at 0° C., and the mixture was stirred at 0° C. for 15 minutes. To this reaction mixture was added the acid chloride solution at 0° C., and the mixture was stirred at room temperature for 13 hours. The reaction mixture was acidified with 1N hydrochloric acid and extracted with chloroform. The organic layer was washed with saturated brine and dried over magnesium sulfate. The solvent was evaporated and the resulting solid was washed with chloroform, to give the entitled compound (338 mg, 73% through the two steps of (d) and (e)).

$^1$H NMR (DMSO-d$_6$) δ 10.47 (s, 1H), 8.78 (s, 1H), 7.81 (d, 2H), 7.09 (d, 2H), 3.94 (s, 1H), 3.84 (s, 3H), 3.56 (s, 1H), 2.44 (d, 1H), 2.12 (d, 1H), 1.60–1.52 (m, 1H), 1.50–1.44 (m, 1H), 1.38–1.30 (m, 1H), 1.23 (d, 1H), 1.05–0.99 (m, 1H).

Example 2

(1R, 3S, 4S)—N-Hydroxy-2-[(4-methoxyphenyl)sulfonyl]-2-azabicyclo[2.2.1]heptane-3-carboxamide (Compound 2)

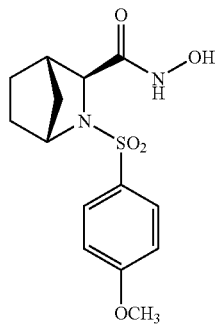

(a) To a solution of ethyl glyoxylate polymer form (45–50% in toluene, 9.36 g) in dichloromethane (82 ml) were added 3A molecular sieves (8.25 g) and (R)-(+)-1-phenylethylamine (5.32 ml, 41.3 mmol) and the mixture was stirred under an argon atmosphere at room temperature for 1 hours. 3A molecular sieves were removed by filtration and the solvent was evaporated.

To the residue dissolved in N,N-dimethylformamide (30 ml) were successively added trifluoroacetic acid (3.18 ml, 41.3 mmol), boron trifluoride diethyl etherate (5.23 ml, 41.3 mmol) and cyclopentadiene (5.09 ml, 45.4 mmol) at 5-minute intervals under an argon atmosphere at –78° C. After being stirred at –78° C. for 2 hours, the reaction mixture was concentrated. The residue, with saturated sodium bicarbonate water added thereto, was extracted with chloroform. The organic layer was washed with saturated brine and dried over magnesium sulfate. The solvent was evaporated and the residue was purified by silica gel column chromatography (5% ethyl acetate/hexane), to give ethyl (1S, 3S, 4R)-2-[(R)-1-phenylethyl]-2-azabicyclo[2.2.1]hept-5-ene-3-carboxylate (5.83 g, 52%).

$^1$H NMR (CDCl$_3$) δ 7.34–7.13 (m, 5H), 6.41 (m, 1H), 6.27 (dd, 1H), 4.30 (s, 1H), 3.81 (m, 2H), 3.03 (q, 1H), 2.90 (brs, 1H), 2.20 (s, 1H), 2.12 (d, 1H), 1.41(d, 4H), 0.95 (t, 3H).

(b) To a solution of ethyl (1S, 3S, 4R)-2-[(R)-1-phenylethyl]-2-azabicyclo[2.2.1]hept-5-ene-3-carboxylate (3.01 g, 11.1 mmol) in ethyl acetate (22 ml) was added 20 wt % Pd(OH)$_2$ (3.89 g) and the mixture was stirred under a hydrogen atmosphere at 45° C. for 60 hours. After a filtration through Celite, the solvent was concentrated. The residue was purified by silica gel column chromatography (1%–2.5% methanol/chloroform), to give ethyl (1R, 3S, 4S)-2-azabicyclo[2.2.1]heptane-3-carboxylate (0.724 g, 39%).

$^1$H NMR (CDCl$_3$) δ 4.18 (q, 2H), 3.53 (s, 1H), 3.30 (s, 1H), 2.62 (s, 1H), 1.68–1.38 (m, 5H), 1.28 (t, 3H), 1.24 (d, 1H).

(c) To a solution of ethyl (1R, 3S, 4S)-2-azabicyclo[2.2.1]heptane-3-carboxylate (0.724 g, 4.28 mmol) in chloroform (8 ml) was added triethylamine (0.60 ml, 4.28 mmol) and 4-methoxybenzenesulfonyl chloride (0.973 g, 4.71 mmol) while being cooled with ice. After a reaction at room temperature for 4 hours, the reaction mixture was washed with 1N hydrochloric acid, saturated sodium bicarbonate water and saturated brine successively, and dried over magnesium sulfate. The solvent was evaporated and the residue was recrystallized (hexane/ethyl acetate), to give ethyl (1R, 3S, 4S)-2-[(4-methoxyphenyl)sulfonyl]-2-azabicyclo[2.2.1]heptane-3-carboxylate (1.04 g, 71%).

$^1$H NMR (CDCl$_3$) δ 7.89 (d, 2H), 6.95 (d, 2H), 4.15–4.05 (m, 3H), 3.93 (s, 1H), 3.86 (s, 3H), 2.70 (d, 1H), 2.04–1.97 (m, 2H), 1.77–1.69 (m, 1H), 1.56–1.45 (m, 2H), 1.32 (d, 1H), 1.22 (t, 3H).

(d) To a solution of ethyl (1R, 3S, 4S)-2-[(4-methoxyphenyl)sulfonyl]-2-azabicyclo[2.2.1]heptane-3-carboxylate (1.04 g, 3.06 mmol) in tetrahydrofuran (20 ml)-methanol(15 ml) was added 1N sodium hydroxide (17 ml), and the mixture was stirred at room temperature for 3 hours. The reaction mixture was acidified with 1N hydrochloric acid and extracted with ethyl acetate. The organic layer was washed with saturated brine and dried over magnesium sulfate. The solvent was evaporated, to give (1R, 3S, 4S)-2-[(4-methoxyphenyl)sulfonyl]-2-azabicyclo[2.2.1]heptane-3-carboxylic acid.

$^1$H NMR (CDCl$_3$) δ 7.87 (d, 2H), 6.98 (d, 2H), 4.12 (s, 1H), 3.92 (s, 1H), 3.88 (s, 3H), 2.85 (d, 1H), 1.98–1.86 (m, 2H), 1.77–1.69 (m, 1H), 1.51–1.43 (m, 1H), 1.40–1.33 (m, 2H).

(e) To a solution of (1R, 3S, 4S)-2-[(4-methoxyphenyl)sulfonyl]-2-azabicyclo[2.2.1]heptane-3-carboxylic acid (1.07 g, 3.44 mmol) in dichloromethane (13 ml) were added oxalyl chloride (0.63 ml, 7.22 mmol) and N,N-dimethylformamide (0.27 ml, 3.44 mmol) while being cooled with ice, and the mixture was stirred at room temperature for 30 minutes. Separately, to a suspension of hydroxylamine hydrochloride (0.955 g, 13.8 mmol) in tetrahydrofuran (4.2 ml)-water (0.84 ml) was added triethylamine (2.92 ml, 21.0 mmol) at 0° C., and the mixture was stirred at 0° C. for 15 minutes. To this reaction mixture was added the acid chloride solution at 0° C., and the mixture was stirred at room temperature for 13 hours. The reaction mixture was acidified with 1N hydrochloric acid and extracted with chloroform. The organic layer was washed with saturated brine and dried over magnesium sulfate. The solvent was evaporated and the resulting solid was washed with chloroform, to give the entitled compound (0.608 g, 61% through the two steps of (d) and (e)).

$^1$H NMR (DMSO-d$_6$) δ 10.47 (s, 1H), 8.79 (s, 1H), 7.82 (d, 2H), 7.10 (d, 2H), 3.95 (s, 1H), 3.85 (s, 3H), 3.56 (s, 1H), 2.45 (d, 1H), 2.13 (d, 1H), 1.62–1.53 (m, 1H), 1.51–1.45 (m, 1H), 1.39–1.32 (m, 1H), 1.25 (d, 1H), 1.06–1.00 (m, 1H).

Example 3

(1S, 3R, 4R)—N-Hydroxy-2-[(4-methoxyphenyl) sulfonyl]-2-azabicyclo[2.2.1]heptane-3-carboxamide (Compound 3)

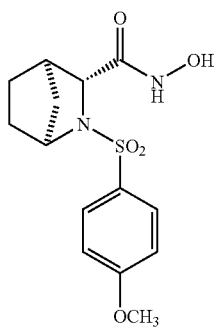

(a) To a solution of ethyl glyoxylate polymer form (45–50% in toluene, 9.36 g) in dichloromethane (82 ml) were added 3A molecular sieves (8.25 g) and (S)-(-)-phenylethylamine (5.32 ml, 41.3 mmol), and the mixture was stirred under an argon atmosphere at room temperature for 1 hour. 3A molecular sieves were removed by filtration and the solvent was evaporated.

To the residue dissolved in N,N-dimethylformamide (30 ml) were successively added trifluoroacetic acid (3.18 ml, 41.3 mmol), boron trifluoride diethyl etherate (5.23 ml, 41.3 mmol) and cyclopentadiene (9.26 ml, 82.5 mmol) at 5 minutes intervals under an argon atmosphere at −78° C. After being stirred at −78° C. for 2 hours, the reaction mixture was concentrated. The residue, with saturated sodium bicarbonate water added thereto, was extracted with chloroform. The organic layer was washed with saturated brine and dried over magnesium sulfate. The solvent was evaporated and the residue was purified by silica gel column chromatography (5% ethyl acetate/hexane), to give ethyl (1R, 3R, 4S)-2-[(S)-1-phenylethyl]-2-azabicyclo[2.2.1]hept-5-ene-3-carboxylate (8.77 g, 78%).

$^1$H NMR (CDCl$_3$) δ 7.34–7.14 (m, 5H), 6.41 (m, 1H), 6.27 (dd, 1H), 4.30 (s, 1H), 3.81 (m, 2H), 3.03 (q, 1H), 2.90 (brs, 1H), 2.20 (s, 1H), 2.12 (d, 1H), 1.41(d, 4H), 0.95 (t, 3H).

(b) To a solution of ethyl (1R, 3R, 4S)-2-[(S)-1-phenylethyl]-2-azabicyclo[2.2.1]hept-5-ene-3-carboxylate (3.84 g, 14.2 mmol) in ethyl acetate (28 ml) was added 20 wt % Pd(OH)$_2$ (4.97 g), and the mixture was stirred under a hydrogen atmosphere at 45° C. 64 hours. After a filtration through Celite, the solvent was concentrated. The residue was purified by silica gel column chromatography (1%–5% methanol/chloroform), to give ethyl (1S, 3R, 4R)-2-azabicyclo[2.2.1]heptane-3-carboxylate (0.595 g, 25%).

$^1$H NMR (CDCl$_3$) δ 4.18 (q, 2H), 3.54 (s, 1H), 3.32 (s, 1H), 2.62 (s, 1H), 1.65–1.38 (m, 5H), 1.28 (t, 3H), 1.24 (d, 1H).

(c) To a solution of ethyl (1S, 3R, 4R)-2-azabicyclo[2.2.1]heptane-3-carboxylate (807 mg, 4.77 mmol) in chloroform (8 ml) were added triethylamine (0.67 ml, 4.77 mmol) and 4-methoxybenzenesulfonyl chloride (1.08 g, 5.25 mmol) while being cooled with ice. After a reaction at room temperature for 4 hours, the reaction mixture was washed with 1N hydrochloric acid, saturated sodium bicarbonate water and saturated brine successively, and dried over magnesium sulfate. The solvent was evaporated and the residue was recrystallized (hexane/ethyl acetate), to give ethyl (1S, 3R, 4R)-2-[(4-methoxyphenyl) sulfonyl]-2-azabicyclo[2.2.1]heptane-3-carboxylate (0.965 g, 60%).

$^1$H NMR (CDCl$_3$) δ 7.89 (d, 2H), 6.95 (d, 2H), 4.13–4.06 (m, 3H), 3.93 (s, 1H), 3.86 (s, 3H), 2.70 (d, 1H), 2.04–1.97 (m, 2H), 1.77–1.69 (m, 1H), 1.56–1.45 (m, 2H), 1.31 (d, 1H), 1.22 (t, 3H).

(d) To a solution of ethyl (1S, 3R, 4R)-2-[(4-methoxyphenyl)sulfonyl]-2-azabicyclo[2.2.1]heptane-3-carboxylate (965 mg, 2.84 mmol) in tetrahydrofuran (40 ml)-methanol (10 ml) was added 1N sodium hydroxide (16 ml), and the mixture was stirred at room temperature for 3 hours. The reaction mixture was acidified with 1N hydrochloric acid and extracted with ethyl acetate. The organic layer was washed with saturated brine and dried over magnesium sulfate. The solvent was evaporated, to give (1S, 3R, 4R)-2-[(4-methoxyphenyl)sulfonyl]-2-azabicyclo[2.2.1]heptane-3-carboxylic acid.

$^1$H NMR (CDCl$_3$) δ 7.88 (d, 2H), 6.98 (d, 2H), 4.12 (s, 1H), 3.92 (s, 1H), 3.88 (s, 3H), 2.85 (d, 1H), 1.99–1.86 (m, 2H), 1.77–1.69 (m, 1H), 1.51–1.43 (m, 1H), 1.41–1.35 (m, 2H).

(e). To a solution of (1S, 3R, 4R)-2-[(4-methoxyphenyl) sulfonyl]-2-azabicyclo[2.2.1]heptane-3-carboxylic acid (667 mg, 2.14 mmol) in dichloromethane (8.2 ml) were added oxalyl chloride (0.39 ml, 4.50 mmol) and N,N-dimethylformamide (0.17 ml, 2.14 mmol) while being cooled with ice, and the mixture was stirred at room temperature for 30 minutes. Separately, to a suspension of hydroxylamine hydrochloride (595 mg, 8.57 mmol) in tetrahydrofuran (2.6 ml)-water (0.5 ml) was added triethylamine (1.82 ml, 13.1 mmol) at 0° C., the mixture was stirred at 0° C. for 15 minutes. To this reaction mixture was added the acid chloride solution at 0° C., and the mixture was stirred at room temperature for 13 hours. The reaction mixture was acidified with 1N hydrochloric acid and extracted with chloroform. The organic layer was washed with saturated brine and dried over magnesium sulfate. The solvent was evaporated and the resulting white solid was washed with chloroform, to give the entitled compound (389 mg, 62% through the two steps of (d) and (e)).

$^1$H NMR (DMSO-d$_6$) δ 10.47 (s, 1H), 8.79 (s, 1H), 7.82 (d, 2H), 7.10 (d, 2H), 3.95 (s, 1H), 3.85 (s, 3H), 3.56 (s, 1H), 2.45 (d, 1H), 2.13 (d, 1H), 1.62–1.53 (m, 1H), 1.51–1.45 (m, 1H), 1.40–1.32 (m, 1H), 1.25 (d, 1H), 1.06–1.00 (m, 1H).

Example 4

(1S, 3R, 4R)—N-Hydroxy-2-[(S)-1-phenylethyl]-2-azabicyclo[2.2.1]heptane-3-carboxamide (Compound 4)

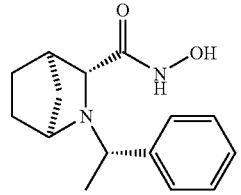

(a) To a solution of ethyl (1R, 3R, 4S)-2-[(S)-1-phenylethyl]-2-azabicyclo[2.2.1]hept-5-ene-3-carboxylate (791 mg, 2.91 mmol) obtained in Example 3 (a) in ethyl acetate (15 ml) was added 10% Pd—C (53 mg), and the mixture was stirred under a hydrogen atmosphere at room temperature for 16 hours. After a filtration through Celite, the solvent was concentrated. The residue was purified by silica gel column chromatography (5% ethyl acetate/hexane), to give ethyl (1S, 3R, 4R)-2-[(S)-1-phenylethyl]-2-azabicyclo[2.2.1]heptane-3-carboxylate (601 mg, 76%).

$^1$H NMR (CDCl$_3$) δ 7.33–7.14 (m, 5H), 3.75 (s, 1H), 3.70 (m, 2H), 3.50 (q, 1H), 2.55 (s, 1H), 2.28 (d, 1H), 2.13 (m, 1H), 2.00 (m, 1H), 1.65 (m, 1H), 1.44–1.28 (m, 6H), 0.92 (t, 3H).

(b) To a solution of ethyl (1S, 3R, 4R)-2-[(S)-1-phenylethyl]-2-azabicyclo[2.2.1]heptane-3-carboxylate (601 mg, 2.20 mmol) in tetrahydrofuran (12 ml)-methanol (6 ml) was added 1N sodium hydroxide (12 ml) and the mixture was stirred at 65° C. for 21 hours. The reaction mixture was neutralized and the water phase was concentrated. The residue was dissolved in chloroform and dried over magnesium sulfate. The solvent was evaporated and the residue was purified by silica gel column chromatography (0–15% methanol/chloroform), to give (1S, 3R, 4R)-2-[(S)-1-phenylethyl]-2-azabicyclo[2.2.1]heptane-3-carboxylic acid (445 mg, 83%).

$^1$H NMR (CDCl$_3$) δ 7.41–7.28 (m, 5H), 4.20 (s, 1H), 3.88 (q, 1H), 3.08 (s, 1H), 2.80 (d, 1H), 2.11–2.03 (m, 1H), 1.95 (d, 1H), 1.89–1.81 (m, 1H), 1.68–1.53 (m, 5H), 1.47 (d, 1H).

(c) To a solution of (1S, 3R, 4R)-2-[(S)-1-phenylethyl]-2-azabicyclo[2.2.1]heptane-3-carboxylic acid (224 mg, 0.913 mmol) in dichloromethane (3.5 ml) were added oxalyl chloride (0.17 ml, 1.92 mmol) and N,N-dimethylformamide (0.07 ml, 0.913 mmol) while being cooled with ice, and the mixture was stirred at room temperature for 30 minutes. Separately, to a suspension of hydroxylamine hydrochloride (254 mg, 3.65 mmol) in tetrahydrofuran (1.0 ml)-water (0.2 ml) was added triethylamine (0.78 ml, 5.57 mmol) at 0° C., and the mixture was stirred at 0° C. for 15 minutes. To this reaction mixture was added the acid chloride solution at 0° C., and the mixture was stirred at room temperature for 14 hours. The reaction mixture, with water added thereto, was extracted with chloroform. The organic layer was washed with saturated brine and dried over magnesium sulfate. The solvent was evaporated, and the residue was purified by silica gel column chromatography (1% methanol/chloroform), to give the entitled compound (126 mg, 53%).

$^1$H NMR (CDCl$_3$) δ7.30–7.19 (m, 5H), 3.64 (s, 1H), 3.44 (q, 1H), 2.68 (s, 1H), 2.38 (d, 1H), 2.04–1.98 (m, 1H), 1.74–1.63 (m, 2H), 1.46–1.37 (m, 5H), 1.24 (d, 1H).

Example 5

N-Hydroxy-2-(4-methoxybenzoyl)-2-azabicyclo[2.2.1]heptane-3-carboxamide (Compound 5)

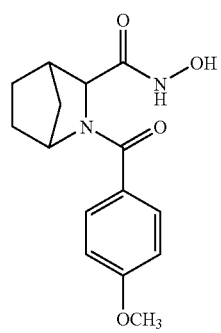

(a) To a solution of ethyl 2-azabicyclo[2.2.1]heptane-3-carboxylate (181 mg, 1.07 mmol) obtained in Example 1 (b) in chloroform (2 ml) were added triethylamine (0.16 ml, 1.18 mmol) and 4-methoxybenzoyl chloride (201 mg, 1.18 mmol) while being cooled with ice. After a reaction at room temperature for 1 hour, the reaction mixture was washed with 1N hydrochloric acid, saturated sodium bicarbonate water and saturated brine successively, and dried over magnesium sulfate. The solvent was evaporated and the residue was purified by silica gel column chromatography (25%–40% ethyl acetate/hexane), to give ethyl 2-(4-methoxybenzoyl)-2-azabicyclo[2.2.1]heptane-3-carboxylate (239 mg, 74%).

$^1$H NMR (CDCl$_3$) δ 7.51 (d, 2H), 6.91 (d, 2H), 4.34 (s, 1H), 4.22 (q, 2H), 4.15 (s, 1H), 3.84 (s, 3H), 2.76 (d, 1H), 2.16 (d, 1H), 1.83–1.60 (m, 4H), 1.34–1.24 (m, 4H).

(b) To a solution of ethyl 2-(4-methoxybenzoyl)-2-azabicyclo[2.2.1]heptane-3-carboxylate (239 mg, 0.787 mmol) in tetrahydrofuran (5 ml)-methanol (4 ml) was added 1N sodium hydroxide (5 ml), and the mixture was stirred at room temperature for 3 hours. The reaction mixture was acidified with 1N hydrochloric acid and extracted with ethyl acetate. The organic layer was washed with saturated brine and dried over magnesium sulfate. The solvent was evaporated, to give 2-(4-methoxybenzoyl)-2-azabicyclo[2.2.1]heptane-3-carboxylic acid.

(c) To a solution was 2-(4-methoxybenzoyl)-2-azabicyclo[2.2.1]heptane-3-carboxylic acid (217 mg, 0.787 mmol) in dichloromethane (3.0 ml) were added oxalyl chloride (0.14 ml, 1.65 mmol) and N,N-dimethylformamide (0.06 ml, 0.787 mmol) while being cooled with ice, and the mixture was stirred at room temperature for 30 minutes. Separately, to a suspension of hydroxylamine hydrochloride (219 mg, 3.15 mmol) in tetrahydrofuran (1.0 ml)-water (0.2 ml) was added triethylamine (0.67 ml, 4.80 mmol) at 0° C., and the mixture was stirred at 0° C. for 15 minutes. To this reaction mixture was added the acid chloride solution at 0° C., and the mixture was stirred at room temperature for 4 hours. The reaction mixture was acidified with 1N hydrochloric acid and extracted with chloroform. The organic layer was washed with saturated brine and dried over magnesium sulfate. The solvent was evaporated, and the resulting residue was purified by silica gel column chromatography (2.5%–10% methanol/chloroform), to give the entitled compound (69.4 mg, 30% through the two steps of (b) and (c)).

$^1$H NMR (CDCl$_3$) δ 10.12 (brs, 1H), 7.52 (d, 2H), 6.91 (d, 2H), 4.33 (s, 1H), 4.17 (s, 1H), 3.84 (s, 3H), 2.94 (s, 1H), 2.21 (d, 1H), 1.74 (m, 1H), 1.58–1.49 (m, 3H), 1.40 (d, 1H).

Example 6

N-Hydroxy-2-(4-methoxybenzyl)-2-azabicyclo[2.2.1]heptane-3-carboxamide (Compound 6)

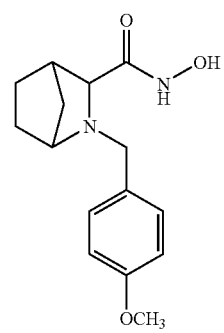

(a) To a solution of ethyl 2-azabicyclo[2.2.1]heptane-3-carboxylate (231 mg, 1.37 mmol) in chloroform (5 ml) were added triethylamine (0.20 ml, 1.43 mmol) and 4-methoxybenzyl chloride (0.19 ml, 1.43 mmol) while being cooled with ice. After a reaction at 60° C. for 20 hours, the reaction mixture, with water added thereto, was extracted with chloroform. The organic layer was washed with saturated brine and dried over magnesium sulfate. The solvent was evaporated and the residue was purified by silica gel column chromatography (1% methanol/chloroform), to give ethyl 2-(4-methoxybenzyl)-2-azabicyclo[2.2.1]heptane-3-carboxylate (340 mg, 86%).

$^1$H NMR (CDCl$_3$) δ 7.26 (d, 2H), 6.81 (d, 2H), 4.00 (q, 2H), 3.78 (s, 3H), 3.67 (s, 2H), 3.32 (s, 1H), 2.64 (s, 1H), 2.50 (d, 1H), 2.03–1.96 (m, 1H), 1.93 (d, 1H), 1.65 (m, 1H), 1.41–1.31 (m, 2H), 1.23 (d, 1H), 1.13 (t, 3H).

(b) To a solution of ethyl 2-(4-methoxybenzyl)-2-azabicyclo[2.2.1]heptane-3-carboxylate (340 mg, 1.18 mmol) in tetrahydrofuran (8 ml)-methanol (4 ml) was added 1N sodium hydroxide (8 ml), and the mixture was stirred at room temperature for 2 hours. The reaction mixture was neutralized with 1N hydrochloric acid and then concentrated. The resulting white solid was washed with chloroform and then filtered. The filtrate was dried over magnesium sulfate and the solvent was evaporated, to give 2-(4-methoxybenzyl)-2-azabicyclo[2.2.1]heptane-3-carboxylic acid.

$^1$H NMR (DMSO-d$_6$) δ 7.40 (d, 2H), 6.90 (d, 2H), 3.99 (s, 2H), 3.76 (s, 1H), 3.75 (s, 3H), 3.12 (s, 1H), 2.58 (d, 1H), 2.05 (m, 1H), 1.71–1.50 (m, 4H), 1.44 (d, 1H).

(c) To a solution of 2-(4-methoxybenzyl)-2-azabicyclo[2.2.1]heptane-3-carboxylic acid (297 mg, 1.14 mmol) in dichloromethane (4.4 ml) were added oxalyl chloride (0.21 ml, 2.34 mmol) and N,N-dimethylformamide (0.09 ml, 1.14 mmol) while being cooled with ice, and the mixture was stirred at room temperature for 30 minutes. Separately, to a suspension of hydroxylamine hydrochloride (316 mg, 4.55 mmol) in tetrahydrofuran (1.5 ml)-water (0.3 ml) was added triethylamine (0.97 ml, 6.94 mmol) at 0° C., and the mixture was stirred at 0° C. for 15 minutes. To this reaction mixture was added the acid chloride solution at 0° C., and the mixture was stirred at room temperature for 15 hours. The reaction mixture, with water added thereto, was extracted with ethyl acetate. The organic layer was washed with saturated brine and dried over magnesium sulfate. The solvent was evaporated and the resulting residue was purified by silica gel column chromatography (2% methanol/chloroform), to give the entitled compound (152 mg, 47% through the two steps of (b) and (c)).

$^1$H NMR (DMSO-d$_6$) δ 9.81 (brs, 1H), 8.59 (brs, 1H), 7.32 (d, 2H), 6.85 (d, 2H), 3.73 (s, 3H), 3.54 (dd, 2H), 3.07 (s, 1H), 2.53 (s, 1H), 2.33 (d, 1H), 1.91 (m, 1H), 1.66 (d, 1H), 1.59 (m, 1H), 1.36 (m, 1H), 1.21 (m, 1H), 1.14 (d, 1H).

Example 7

(3R)—N-Hydroxy-2-[(4-methoxyphenyl)sulfonyl]-2-azabicyclo[2.2.2]octane-3-carboxamide (Compound 7)

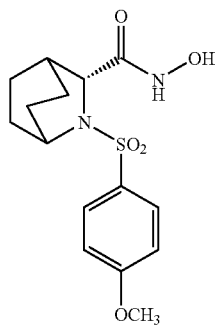

(a) To a solution of ethyl glyoxylate polymer form (45–50% in toluene, 4.54 g) in chloroform (40 ml) were added 3A molecular sieves (4.00 g) and (S)-(−)-phenylethylamine (2.58 ml, 20.0 mmol), and the mixture was stirred under an argon atmosphere at room temperature for 1 hour. 3A molecular sieves were removed by filtration, and then the solvent was evaporated.

To the residue dissolved in N,N-dimethylformamide (14 ml) were successively added trifluoroacetic acid (1.54 ml, 20.0 mmol), boron trifluoride diethyl etherate (2.53 ml, 20.0 mmol) and 1,3-cyclohhexadiene (2.86 ml, 30.0 mmol) at 5-minutes intervals under an argon atmosphere at −78° C. After being stirred at room temperature for 5 hours, the reaction mixture was concentrated. The residue, with saturated sodium bicarbonate water added thereto, was extracted with ethyl acetate. The organic layer was washed with saturated brine and dried over magnesium sulfate. The solvent was evaporated and the residue was purified by silica gel column chromatography (2% ethyl acetate/hexane), to give ethyl (1R, 3R, 4S)-2-[(S)-1-phenylethyl]-2-azabicyclo[2.2.2]oct-5-ene-3-carboxylate (1.20 g, 21%).

$^1$H NMR (CDCl$_3$) δ 7.40 (d, 2H), 7.27–7.16 (m, 3H), 6.39 (m, 1H), 6.26 (m, 1H), 3.97 (q, 2H), 3.62 (m, 1H), 3.43 (q, 1H), 2.89 (m, 1H), 2.72 (m, 1H), 2.03 (m, 1H), 1.59 (m, 1H), 1.32–1.24 (m, 1H), 1.29 (d, 3H), 1.12 (t, 3H), 1.02 (m, 1H).

(b) To a solution of ethyl (1R, 3R, 4S)-2-[(S)-1-phenylethyl]-2-azabicyclo[2.2.2]oct-5-ene-3-carboxylate (1.20 g, 4.17 mmol) in ethyl acetate (52 ml) was added 20 wt % Pd(OH)$_2$ (0.878 g), and the mixture was stirred under a hydrogen atmosphere at 45° C. for 14 hours. After a filtration through Celite, the solvent was concentrated. The residue was purified by silica gel column chromatography (1%–5% methanol/chloroform), to give ethyl (3R)-2-azabicyclo[2.2.2]octane-3-carboxylate (0.362 g, 47%).

$^1$H NMR (CDCl$_3$) δ 4.28–4.15 (m, 2H), 3.71 (brs, 1H), 2.91 (brs, 1H), 2.10 (br, 1H), 2.00 (m, 1H), 1.89–1.48 (m, 8H), 1.28 (t, 3H).

(c) To a solution of ethyl (3R)-2-azabicyclo[2.2.2]octane-3-carboxylate (362 mg, 1.97 mmol) in chloroform (4.0 ml) were added triethylamine (0.30 ml, 2.17 mmol) and 4-methoxybenzenesulfonyl chloride(448 mg, 2.17 mmol) while being cooled with ice. After a reaction at room temperature for 2 hours, the reaction mixture was washed with 1N hydrochloric acid, saturated sodium bicarbonate water and saturated brine successively, and dried over magnesium sulfate. The solvent was evaporated and the residue was recrystallized (hexane/ethyl acetate), to give ethyl (3R)-2-[(4-methoxyphenyl)sulfonyl]-2-azabicyclo[2.2.2]octane-3-carboxylate (261 mg). Further, mother liquid was concentrated, and the resulting residue was purified by silica gel column chromatography (1%–5% methanol/chloroform), to give the same compound (137 mg, total 399 mg, 57%).

$^1$H NMR (CDCl$_3$) δ 7.95 (d, 2H), 6.96 (d, 2H), 4.34 (d, 1H), 4.22 (q, 2H), 3.89 (s, 3H), 3.58 (d, 1H), 2.22 (m, 1H), 1.99 (m, 1H), 1.83 (m, 1H), 1.69–1.38 (m, 6H), 1.29 (t, 3H).

(d) To a solution of ethyl (3R)-2-[(4-methoxyphenyl)sulfonyl]-2-azabicyclo[2.2.2]octane-3-carboxylate (399 mg, 1.13 mmol) in tetrahydrofuran (7 ml)-methanol (4 ml) was added 1N sodium hydroxide (7 ml), and the mixture was stirred at 65° C. for 12 hours. The reaction mixture was acidified with 1N hydrochloric acid and extracted with ethyl acetate. The organic layer was washed with saturated brine and dried over magnesium sulfate. The solvent was evaporated, to give (3R)-2-[(4-methoxyphenyl)sulfonyl]-2-azabicyclo[2.2.2]octane-3-carboxylic acid.

$^1$H NMR (CDCl$_3$) δ 7.91 (d, 2H), 6.98 (d, 2H), 4.32 (d, 1H), 3.88 (s, 3H), 3.66 (d, 1H), 2.29 (d, 1H), 2.00 (m, 1H), 1.79–1.39 (m, 7H).

(e) To a solution of (3R)-2-[(4-methoxyphenyl)sulfonyl]-2-azabicyclo[2.2.2]octane-3-carboxylic acid (343 mg, 1.06 mmol) in dichloromethane (4.0 ml) were added oxalyl chloride (0.19 ml, 2.21 mmol) and N,N-dimethylformamide (0.08 ml, 1.06 mmol) while being cooled with ice, and the mixture was stirred at room temperature for 30 minutes. Separately, to a suspension of hydroxylamine hydrochloride (293 mg, 4.22 mmol) in tetrahydrofuran (1.5 ml)-water (0.3 ml) was added triethylamine (0.90 ml, 6.44 mmol) at 0° C., and the mixture was stirred at 0° C. for 15 minutes. To this reaction mixture was added the acid chloride solution at 0° C., and the mixture was stirred at room temperature for 15 hours. The reaction mixture was acidified with 1N hydrochloric acid and extracted with chloroform. The organic layer was washed with saturated sodium bicarbonate water and saturated brine, successively, and dried over magnesium sulfate. The solvent was evaporated and the resulting white solid was washed with chloroform, to give the entitled compound (75 mg, 19% through the two steps of (d) and (e)).

$^1$H NMR (DMSO-d$_6$) δ 10.42 (s, 1H), 8.77 (s, 1H), 7.86 (d, 2H), 7.10 (d, 2H), 3.95 (d, 1H), 3.85 (s, 3H), 3.53 (d, 1H), 1.99 (m, 1H), 1.92 (brs, 1H), 1.68 (m, 1H), 1.55–1.26 (m, 5H), 1.14 (m, 1H).

Example 8

(1S, 3R, 4R)—N-Hydroxy-2-(phenylsulfonyl)-2-azabicyclo[2.2.1]heptane-3-carboxamide (Compound 8)

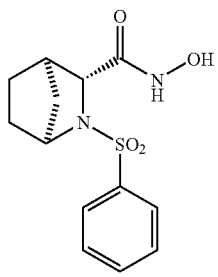

(a) To a solution of ethyl (1S, 3R, 4R)-2-azabicyclo[2.2.1]heptane-3-carboxylate (152 mg, 0.897 mmol) obtained in Example 3 (b) in chloroform (4.5 ml) were added triethylamine (0.13 ml, 0.942 mmol) and benzenesulfonyl chloride (0.12 ml, 0.942 mmol) while being cooled with ice. After a reaction at room temperature for 2 hours, the reaction mixture was washed with 1N hydrochloric acid, saturated sodium bicarbonate water and saturated brine successively, and dried over magnesium sulfate, and the solvent was evaporated.

(b) To the residue dissolved in tetrahydrofuran (8 ml)-methanol (4 ml) was added 1N sodium hydroxide (7 ml), and the mixture was stirred at room temperature for 3 hours. The reaction mixture was acidified with 1N hydrochloric acid and extracted with ethyl acetate. The organic layer was dried over magnesium sulfate, and the solvent was evaporated.

(c) To the residue dissolved in dichloromethane (3.9 ml) were added oxalyl chloride (0.19 ml, 2.14 mmol) and N,N-dimethylformamide (0.08 ml, 1.02 mmol) while being cooled with ice, and the mixture was stirred at room temperature for 30 minutes. Separately, to a suspension of hydroxylamine hydrochloride (284 mg, 4.08 mmol) in tetrahydrofuran (1.5 ml)-water (0.3 ml) was added triethylamine (0.87 ml, 6.23 mmol) at 0° C., and the mixture was stirred at 0° C. for 15 minutes. To this reaction mixture was added the acid chloride solution at 0° C., and the mixture was stirred at room temperature for 18 hours. The reaction mixture was acidified with 1N hydrochloric acid and extracted with chloroform. The organic layer was washed with saturated brine and dried over magnesium sulfate. The solvent was evaporated and the resulting residue was purified by silica gel column chromatography (chloroform:methanol=40:1–20:1), to give the entitled compound (119 mg, 45% through the three steps of (a), (b) and (c)).

$^1$H NMR (DMSO-d$_6$) δ 10.51 (s, 1H), 9.90 (s, 1H), 7.89 (d, 2H), 7.68 (t, 1H), 7.60 (t, 2H), 3.99 (s, 1H), 3.61 (s, 1H), 2.46 (d, 1H), 2.15 (d, 1H), 1.57 (m, 1H), 1.42–1.34 (m, 2H), 1.26 (d, 1H), 1.01 (m, 1H).

Example 9

(1S, 3R, 4R)-2-[(4-Chlorophenyl)sulfonyl]-N-hydroxy-2-azabicyclo[2.2.1]heptane-3-carboxamide (Compound 9)

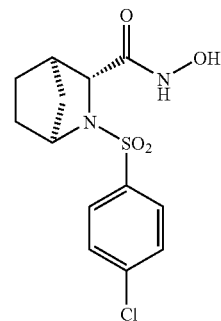

(a) To a solution of ethyl (1S, 3R, 4R)-2-azabicyclo[2.2.1]heptane-3-carboxylate (146 mg, 0.864 mmol) obtained in Example 3 (b) in chloroform (4.3 ml) were added triethylamine (0.13 ml, 0.907 mmol) and 4-chlorobenzenesulfonyl chloride (192 mg, 0.907 mmol) while being cooled with ice. After a reaction at room temperature for 2 hours, the reaction mixture was washed with 1N hydrochloric acid, saturated sodium bicarbonate water and saturated brine successively, and dried over magnesium sulfate, and the solvent was evaporated.

(b) To the residue dissolved in tetrahydrofuran (7 ml)-methanol (4 ml) was added 1N sodium hydroxide (6 ml) and the mixture was stirred at room temperature for 17 hours. The reaction mixture was acidified with 1N hydrochloric acid and extracted with ethyl acetate. The organic layer was dried over magnesium sulfate, and the solvent was evaporated.

(c) To the residue dissolved in dichloromethane (3.8 ml) were added oxalyl chloride (0.18 ml, 2.09 mmol) and N,N-dimethylformamide (0.08 ml, 1.00 mmol) while being cooled with ice, and the mixture was stirred at room temperature for 30 minutes. Separately, to a suspension of hydroxylamine hydrochloride (277 mg, 3.98 mmol) in tetrahydrofuran (1.5 ml)-water (0.3 ml) was added triethylamine (0.85 ml, 6.07 mmol) at 0° C., and the mixture was stirred at 0° C. for 15 minutes. To this reaction mixture was added the acid chloride solution at 0° C., and the mixture was stirred at room temperature for 62 hours. The reaction mixture was acidified with 1N hydrochloric acid and extracted with chloroform. The organic layer was washed with saturated brine and dried over magnesium sulfate. The solvent was evaporated and the resulting white solid was washed with methanol, to give the entitled compound (15 mg, 5% through the three steps of (a), (b) and (c)).

$^1$H NMR (DMSO-d$_6$) δ 10.52 (s, 1H), 8.82 (s, 1H), 7.89 (t, 2H), 7.66 (d, 2H), 4.01 (s, 1H), 3.63 (s, 1H), 2.49 (s, 1H), 2.13 (d, 1H), 1.77 (m, 1H), 1.64–1.20 (m, 3H), 1.11 (m, 1H).

Example 10

(1S, 3R, 4R)-2-{[4-(Acetylamino)phenyl]sulfonyl}-N-hydroxy-2-azabicyclo[2.2.1]heptane-3-carboxamide (Compound 10)

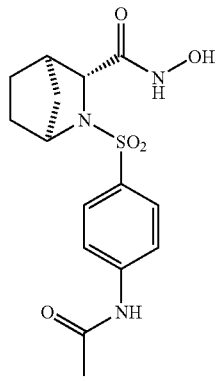

(a) To a solution of ethyl (1S, 3R, 4R)-2-azabicyclo[2.2.1]heptane-3-carboxylate (145 mg, 0.855 mmol) obtained in Example 3 (b) in chloroform (4.3 ml) were added triethylamine (0.13 ml, 0.898 mmol) and 4-acetoamidobenzenesulfonyl chloride (210 mg, 0.898 mmol) while being cooled with ice. After a reaction at room temperature for 2 hours, the reaction mixture was washed with 1N hydrochloric acid and saturated brine successively, and dried over magnesium sulfate, and the solvent was evaporated.

(b) To the residue dissolved in tetrahydrofuran (7 ml)-methanol (4 ml) was added 1N sodium hydroxide (6 ml), and the mixture was stirred at room temperature for 21 hours. The reaction mixture was acidified with 1N hydrochloric acid and extracted with ethyl acetate. The organic layer was dried over magnesium sulfate, and the solvent was evaporated.

(c) To the residue dissolved in dichloromethane (3.7 ml) were added oxalyl chloride (0.17 ml, 2.00 mmol) and N,N-dimethylformamide (0.07 ml, 0.95 mmol) while being cooled with ice, and the mixture was stirred at room temperature for 30 minutes. Separately, to a suspension of hydroxylamine hydrochloride (264 mg, 3.80 mmol) in tetrahydrofuran (1.5 ml)-water (0.3 ml) was added triethylamine (0.81 ml, 5.80 mmol) at 0° C., and the mixture was stirred at 0° C. for 15 minutes. To this reaction mixture was added the acid chloride solution at 0° C., and the mixture was stirred at room temperature for 23 hours. The reaction mixture was acidified with 1N hydrochloric acid and extracted with chloroform. The organic layer was washed with saturated brine and dried over magnesium sulfate. The solvent was evaporated and the resulting white solid was washed with methanol, to give the entitled compound (16 mg, 5% through the three steps of (a), (b) and (c)).

$^1$H NMR (DMSO-d$_6$) δ 10.46 (s, 1H), 10.28 (s, 1H), 8.80 (s, 1H), 7.82–7.75 (m, 4H), 3.97 (s, 1H), 3.56 (s, 1H), 2.45 (s, 1H), 2.13 (d, 1H), 2.09 (s, 3H), 1.56 (m, 1H), 1.47–1.33 (m, 2H), 1.24 (d, 1H), 1.00 (m, 1H).

Example 11

(1S, 3R, 4R)—N-Hydroxy-2-[4-(methylphenyl)sulfonyl]-2-azabicyclo[2.2.1]heptane-3-carboxamide (Compound 11)

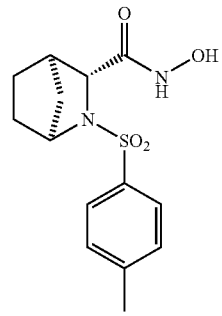

(a) To a solution of ethyl (1S, 3R, 4R)-2-azabicyclo[2.2.1]heptane-3-carboxylate (148 mg, 0.876 mmol) obtained in Example 3 (b) in chloroform (4.4 ml) were added triethylamine (0.13 ml, 0.920 mmol) and p-toluenesulfonyl chloride (175 mg, 0.920 mmol) while being cooled with ice. After a reaction at room temperature for 2 hours, the reaction mixture was washed with 1N hydrochloric acid and saturated brine successively, and dried over magnesium sulfate, and the solvent was evaporated.

(b) To the residue dissolved in tetrahydrofuran (7 ml)-methanol (4 ml) was added 1N sodium hydroxide (7 ml), and the mixture was stirred at room temperature for 3 hours. The reaction mixture was acidified with 1N hydrochloric acid and extracted with ethyl acetate. The organic layer was washed with saturated brine and dried over magnesium sulfate, and the solvent was evaporated.

(c) To the residue dissolved in dichloromethane (3.6 ml) were added oxalyl chloride (0.17 ml, 1.94 mmol) and N,N-dimethylformamide (0.07 ml, 0.92 mmol) while being cooled with ice, and the mixture was stirred at room temperature for 30 minutes. Separately, to a suspension of hydroxylamine hydrochloride (257 mg, 3.69 mmol) in tetrahydrofuran (1.5 ml)-water (0.3 ml) was added triethylamine (0.78 ml, 5.63 mmol) at 0° C., the mixture was stirred at 0° C. for 15 minutes. To this reaction mixture was added the acid chloride solution at 0° C., and the mixture was stirred at room temperature for 24 hours. The reaction mixture was acidified with 1N hydrochloric acid and extracted with chloroform. The organic layer was washed with saturated brine and dried over magnesium sulfate. The solvent was evaporated and the resulting white solid was washed with methanol, to give the entitled compound (72 mg, 25% through the three steps of (a), (b) and (c)).

$^1$H NMR (DMSO-d$_6$) δ 10.49 (s, 1H), 8.81 (s, 1H), 7.77 (d, 2H), 7.39 (d, 2H), 3.97 (s, 1H), 3.59 (s, 1H), 2.45 (d, 1H), 2.40 (s, 3H), 2.14 (d, 1H), 1.57 (m, 1H), 1.43–1.34 (m, 2H), 1.24 (d, 1H), 1.01 (m, 1H).

Example 12

(1S, 3R, 4R)-2-[4-(Butoxyphenyl)sulfonyl]-N-hydroxy-2-azabicyclo[2.2.1]heptane-3-carboxamide (Compound 12)

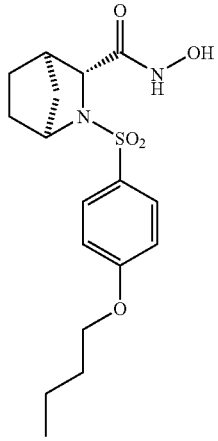

(a) To a solution of ethyl (1S, 3R, 4R)-2-azabicyclo[2.2.1]heptane-3-carboxylate (194 mg, 1.15 mmol) obtained in Example 3 (b) in chloroform (5.7 ml) were added triethylamine (0.17 ml, 1.20 mmol) and 4-(n-butoxy)benzenesulfonyl chloride (300 mg, 1.20 mmol) while being cooled with ice. After a reaction at room temperature for 2 hours, the reaction mixture was washed with 1N hydrochloric acid and saturated brine successively, and dried over magnesium sulfate, and the solvent was evaporated.

(b) To the residue dissolved in tetrahydrofuran (10 ml)-methanol (6 ml) was added 1N sodium hydroxide (10 ml), and the mixture was stirred at room temperature for 17 hours. The reaction mixture was acidified with 1N hydrochloric acid and extracted with ethyl acetate. The organic layer was washed with saturated brine and dried over magnesium sulfate, and the solvent was evaporated.

(c) To the residue dissolved in dichloromethane (4.0 ml) were added oxalyl chloride (0.19 ml, 2.18 mmol) and N,N-dimethylformamide (0.08 ml, 1.04 mmol) while being cooled with ice, and the reaction mixture was stirred at room temperature for 30 minutes. Separately, to a suspension of hydroxylamine hydrochloride (289 mg, 4.16 mmol) in tetrahydrofuran (1.5 ml)-water (0.3 ml) was added triethylamine (0.88 ml, 6.34 mmol) at 0° C., and the mixture was stirred at 0° C. for 15 minutes. To this reaction mixture was added the acid chloride solution at 0° C., and the mixture was stirred at room temperature for 18 hours. The reaction mixture was acidified with 1N hydrochloric acid and extracted with chloroform. The organic layer was washed with saturated brine and dried over magnesium sulfate. The solvent was evaporated and the resulting white solid was washed with methanol, to give the entitled compound (128 mg, 30% through the three steps of (a), (b) and (c)).

$^1$H NMR (DMSO-$d_6$) δ 10.47 (s, 1H), 8.79 (s, 1H), 7.80 (d, 2H), 7.08 (d, 2H), 4.07 (t, 2H), 3.95 (s, 1H), 3.56 (s, 1H), 2.45 (d, 1H), 2.12 (d, 1H), 1.72 (m, 2H), 1.63–1.33 (m, 5H), 1.24 (d, 1H), 1.03 (m, 1H), 0.94 (t, 3H).

Example 13

(1S, 3R, 4R)-2-[(4-Fluorophenyl)sulfonyl]-N-hydroxy-2-azabicyclo[2.2.1]heptane-3-carboxamide (Compound 13)

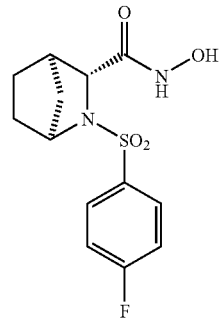

(a) To a solution of ethyl (1S, 3R, 4R)-2-azabicyclo[2.2.1]heptane-3-carboxylate (272 mg, 1.61 mmol) obtained in Example 3 (b) in chloroform (8 ml) were added triethylamine (0.24 ml, 1.69 mmol) and 4-fluorobenzenesulfonyl chloride (329 mg, 1.69 mmol) while being cooled with ice. After a reaction at room temperature for 2 hours, the reaction mixture was washed with 1N hydrochloric acid and saturated brine successively, and dried over magnesium sulfate, and the solvent was evaporated.

(b) To the residue dissolved in tetrahydrofuran (14 ml)-methanol (8 ml) was added 1N sodium hydroxide (14 ml), and the mixture was stirred at room temperature for 16 hours. The reaction mixture was acidified with 1N hydrochloric acid and extracted with ethyl acetate. The organic layer was washed with saturated brine and dried over magnesium sulfate, and the solvent was evaporated.

(c) To the residue dissolved in dichloromethane (4.4 ml) were added oxalyl chloride (0.21 ml, 2.40 mmol) and N,N-dimethylformamide (0.09 ml, 1.14 mmol) while being cooled with ice, and the mixture was stirred at room temperature for 30 minutes. Separately, to a suspension of hydroxylamine hydrochloride (318 mg, 4.58 mmol) in tetrahydrofuran (1.5 ml)-water (0.3 ml) was added triethylamine (0.97 ml, 6.98 mmol) at 0° C., and the mixture was stirred at 0° C. for 15 minutes. To this reaction mixture was added the acid chloride solution at 0° C., and the mixture was stirred at room temperature for 17 hours. The reaction mixture was acidified with 1N hydrochloric acid and extracted with chloroform. The organic layer was washed with saturated brine and dried over magnesium sulfate. The solvent was evaporated and the resulting white solid was washed with methanol, to give the entitled compound (195 mg, 39% through the three steps of (a), (b) and (c)).

$^1$H NMR (DMSO-$d_6$) δ 10.52 (s, 1H), 8.81 (s, 1H), 7.97 (dd, 2H), 7.43 (t, 2H), 4.00 (s, 1H), 3.62 (s, 1H), 2.47 (d, 1H), 2.14 (d, 1H), 1.61 (m, 1H), 1.54–1.38 (m, 2H), 1.27 (d, 1H), 1.10 (m, 1H).

Example 14

5-(tert-Butyl)-(1R, 3R, 4S)—N-hydroxy-2-[(4-methoxyphenyl)sulfonyl]-2-azabicyclo[2.2.1]heptane-3-carboxamide (Compound 14)

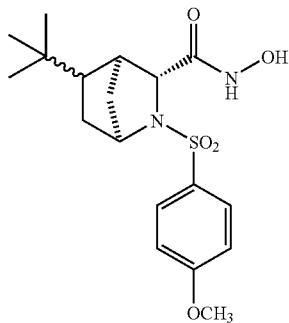

(a) To a solution of ethyl glyoxylate polymer form (45–50% in toluene, 4.68 g) in chloroform (41 ml) were added 3A molecular sieves (4.13 g) and (S)-(−)-phenylethylamine (2.66 ml, 20.6 mmol), and the mixture was stirred under an argon atmosphere at room temperature for 1 hour. 3A molecular sieves was removed by filtration and the solvent was evaporated.

To the residue dissolved in N,N-dimethylformamide (15 ml) were successively added trifluoroacetic acid (1.59 ml, 20.6 mmol), boron trifluoride diethyl etherate (2.62 ml, 20.6 mmol) and tert-butylcyclopentadiene (6.08 ml, 41.3 mmol) at 5-minutes intervals under an argon atmosphere at −78° C. After being stirred at −78° C. for 2 hours, the reaction mixture was concentrated. The residue, with saturated sodium bicarbonate water added thereto, was extracted with ethyl acetate. The organic layer was washed with saturated brine and dried over magnesium sulfate. The solvent was evaporated and the residue was purified by silica gel column chromatography (1%–3% ethyl acetate/hexane), to give ethyl (1R, 3R, 4R)-5-(tert-butyl)-2-[(S)-1-phenylethyl]-2-azabicyclo[2.2.1]hept-5-ene-3-carboxylate (3.41 g, 51%).

$^1$H NMR(CDCl$_3$) δ 7.29–7.13(m, 5H), 5.86(s, 1H), 4.19 (s, 1H), 3.83(q, 2H), 3.11(q, 1H), 2.98(s, 1H), 2.32(s, 1H), 2.13(d, 1H), 1.41(d, 4H), 1.13(s, 9H), 0.95(t, 3H).

(b) To a solution of ethyl (1R, 3R, 4R)-5-(tert-butyl)-2-[(S)-1-phenylethyl]-2-azabicyclo [2.2.1]hept-5-ene-3-carboxylate (1.22 g, 3.74 mmol) in ethyl acetate (43 ml) was added 20 wt % Pd(OH)$_2$ (0.578 g), and the mixture was stirred under a hydrogen atmosphere at 45° C. for 62 hours. After a filtration through Celite, the solvent was evaporated. The residue was purified by silica gel column chromatography (1%–5% methanol/chloroform), to give ethyl (1R, 3R, 4S)-5-(tert-butyl)-2-azabicyclo[2.2.1]heptane-3-carboxylate (0.197 g, 23%).

$^1$H NMR(CDCl$_3$) δ 4.18(q, 2H), 3.50(s, 1H), 3.25(s, 1H), 2.55(s, 1H), 1.60–1.22(m, 8H), 0.87(s, 9H).

(c) To a solution of ethyl (1R, 3R, 4S)-5-(tert-butyl)-2-azabicyclo[2.2.1]heptane-3-carboxylate (182 mg, 0.806 mmol) in chloroform (4.0 ml) were added triethylamine (0.12 ml, 0.846 mmol) and 4-methoxybenzenesulfonyl chloride (175 mg, 0.846 mmol) while being cooled with ice. After a reaction at room temperature for 2 hours, the reaction mixture was washed with 1N hydrochloric acid, saturated sodium bicarbonate water and saturated brine successively, and dried over magnesium sulfate, and the solvent was evaporated.

(d) To the residue dissolved in tetrahydrofuran (10 ml)-methanol (6 ml) was added 1N sodium hydroxide (10 ml), and the mixture was stirred at room temperature for 4 hours. The reaction mixture was acidified with 1N hydrochloric acid and extracted with ethyl acetate. The organic layer was dried over magnesium sulfate, and the solvent was evaporated.

(e) To the residue dissolved in dichloromethane (3.1 ml) were added oxalyl chloride (0.15 ml, 1.70 mmol) and N,N-dimethylformamide (0.06 ml, 0.809 mmol) while being cooled with ice, and the mixture was stirred at room temperature for 30 minutes. Separately, to a suspension of hydroxylamine hydrochloride (225 mg, 3.24 mmol) in tetrahydrofuran (1.0 ml)-water (0.2 ml) was added triethylamine (0.69 ml, 4.93 mmol) at 0° C., and the mixture was stirred at 0° C. for 15 minutes. To this reaction mixture was added the acid chloride solution at 0° C., and the mixture was stirred at room temperature for 15 hours. The reaction mixture was acidified with 1N hydrochloric acid and extracted with chloroform. The organic layer was washed with saturated brine and dried over magnesium sulfate. The solvent was evaporated and the resulting residue was purified by silica gel column chromatography (chloroform:methanol=40:1), to give the entitled compound (175 mg, 57% through the three steps of (a)–(c)).

$^1$H NMR(DMSO-d$_6$) δ 10.49(s, 1H), 8.77(s, 1H), 7.83(d, 2H), 7.10(d, 2H), 3.92(s, 1H), 3.85(s, 3H), 3.57(s, 1H), 2.39(s, 1H), 2.02(d, 1H), 1.64(t, 1H), 1.27(d, 1H), 1.18(m, 1H), 0.99(t, 1H), 0.72(s, 9H).

Further, compounds of the present invention and the producing methods thereof will be exemplified.

Compound 15

N-Hydroxy-2-{[4'-methoxy(1,1'-biphenyl)-4-yl]sulfonyl}-2-azabicyclo[2.2.2]octane-3-carboxamide

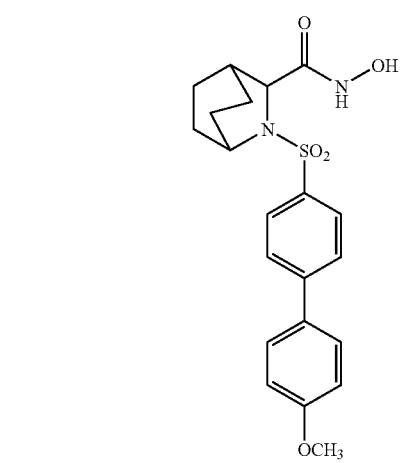

(a) In the reaction (a) of Example 1, 1,3-cyclohexadiene is used in place of cyclopentadiene to give ethyl 2-(1-phenylethyl)-2-azabicyclo[2.2.2]oct-5-ene-3-carboxylate.

(b) Ethyl 2-(1-phenylethyl)-2-azabicyclo[2.2.2]oct-5-ene-3-carboxylate is subjected to a reaction similar to the reaction (b) of Example 1, to give ethyl 2-azabicyclo[2.2.2]octane-3-carboxylate.

(c) Ethyl 2-azabicyclo[2.2.2]octane-3-carboxylate is subjected to a reaction similar to the reaction (c) of Example 1 using [4-(4-methoxyphenyl)phenyl]sulfonyl chloride in place of 4-methoxybenzenesulfonyl chloride, to give ethyl 2-{[4'-methoxy(1,1'-biphenyl)-4-yl]sulfonyl}-2-azabicyclo[2.2.2]octane-3-carboxylate.

(d) Ethyl 2-{[4'-methoxy(1,1'-biphenyl)-4-yl]sulfonyl}-2-azabicyclo[2.2.2]octane-3-carboxylate is subjected to reactions similar to the reactions (d) and (e) of Example 1, to give the entitled compound.

Compound 16

N-Hydroxy-2-[(4-methoxyphenyl)sulfonyl]-2-azabicyclo[2.2.2]octane-3-carboxamide

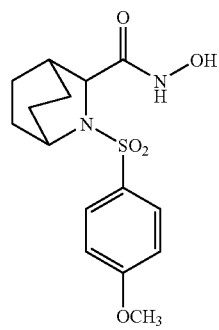

Ethyl 2-azabicyclo[2.2.2]octane-3-carboxylate obtained in Compound 15 (b) is subjected to reactions similar to the reactions (c), (d) and (e) of Example 1, to give the entitled compound.

Compound 17

N-Hydroxy-2-{[4-(4-pyridinyloxy)phenyl]sulfonyl}-2-azabicyclo[2.2.1]heptane-3-carboxamide

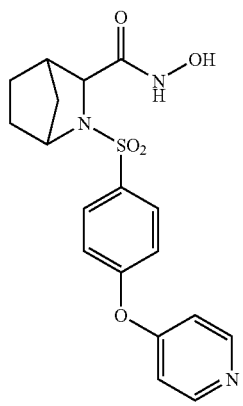

(a) Ethyl 2-azabicyclo[2.2.1]heptane-3-carboxylate obtained in Example 1 (b) is subjected to a reaction similar to the reaction (c) of Example 1 using [4-(4-pyridyloxy)phenyl]sulfonyl chloride hydrochloride in place of 4-methoxybenzenesulfonyl chloride, to give ethyl 2-{[4-(4-pyridyloxy)phenyl]sulfonyl}-2-azabicyclo[2.2.1]heptane-3-carboxylate.

(b) Ethyl 2-{[4-(4-pyridyloxy)phenyl]sulfonyl}-2-azabicyclo[2.2.1]heptane-3-carboxylate is subjected to reactions similar to the reactions (d) and (e) of Example 1, to give the entitled compound.

Compound 18

N-Hydroxy-6-(1-phenylethyl)-6-azabicyclo[3.2.2]non-8-ene-7-carboxamide

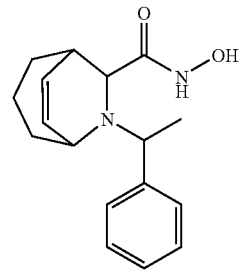

(a) In the reaction (a) of Example 1, 1,3-cycloheptadiene is used in place of cyclopentadiene, to give ethyl 6-(1-phenylethyl)-6-azabicyclo[3.2.2]non-8-ene-7-carboxylate.

(b) Ethyl 6-(1-phenylethyl)-6-azabicyclo[3.2.2]non-8-ene-7-carboxylate is subjected to reactions similar to reactions (d) and (e) of Example 1, to give the entitled compound.

Compound 19

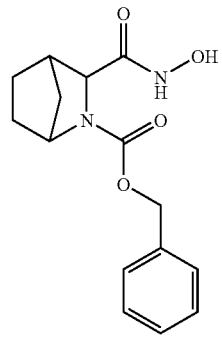

Compound 20

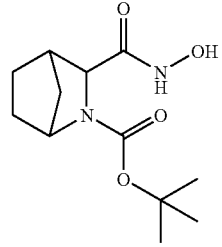

Compound 21

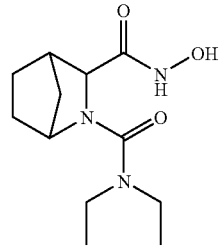

Compounds 19–21 can be also produced according to methods described above. For example, Compounds 19 and 20 can be produced by a method according to Example 5 using benzyloxycarbonyl chloride and t-butyloxycarbonyl chloride, respectively. Compound 21 can be produced using diethylaminocarbonyl chloride.

Further, not only the compounds described above but also other compounds of the present invention can be produced according to methods described above or known methods.

Compound (I) of the present invention, unless there is any problem, may have a substituent on the azabicyclo ring. Such a compound can be obtained by using a diene having the desired substituent. Also, it is possible that a diene having a functional group that can be converted into the desired substituent is used and the functional group is converted into the desired substituent at a suitable step. Furthermore, the desired substituent can be introduced due to the reactivity of the double bond on the azabicyclo ring. These reactions can be performed by known methods alone or in combination.

The substituent on the azabicyclo ring includes the following groups $R^A$ and $R^B$.

$R^A$: hydrogen atom, halogen atom, nitro, cyano, acyl, carbamoyl, oxo (=O), thioxo (=S), imino (=NH), $COOR^3$, or $=CR^4R^5$.

$R^B$: hydrogen atom, alkyl, heteroalkyl, aryl, heteroaryl, amino, mercapto, $OR^7$ or $SO_2R^8$.

$R^4$ and $R^5$ each can be hydrogen atom, halogen atom, alkyl, heteroalkyl, aryl, heteroaryl, acyl, carbamoyl or $COOR^6$.

$R^3$, $R^6$ and $R^7$ each can be hydrogen atom, alkyl, heteroalkyl, aryl, heteroaryl, arylalkyl or heteroarylalkyl.

$R^8$ can be alkyl, heteroalkyl, aryl or heteroaryl.

There can be more then one $R^A$ or $R^B$ respectively. When X is methylene or ethylene and R is $SO_2R^2$ and $R^A$ are all hydrogen atoms, $R^B$ is preferably hydrogen atom, alkyl, heteroalkyl, aryl or heteroaryl. Also, when X is propylene and R is acyl, $COOR^1$, carbamoyl or $SO_2R^2$, $R^A$ is preferably halogen atom, nitro, cyano, acyl, $COOR^3$, carbamoyl, $=CR^4R^5$, thioxo or imino.

Also, when $R^A$ and $R^B$ each are bonded to different atoms in the azabicyclo ring, $R^A$ and $R^B$ may form a 3- to 6-memberd ring together with the atoms to which $R^A$ and $R^B$ bonded. This 3- to 6-memberd ring may contain one or two heteroatoms selected from N, O and S. Further, this 3- to 6-memberd ring may be substituted by at least one substituent at a feasible position. Such a substituent can be selected from the group of alkyl, heteroalkyl, aryl, heteroaryl, arylalkyl, heteroarylalkyl, oxo, halogen atom, hydroxy and alkoxy.

The amino group may be an unsubstituted or substituted amino group. The substituted amino group includes an amino group having one or two substituents selected from the group of alkyl, heteroalkyl, aryl, heteroaryl, arylalkyl, heteroarylalkyl, $OR^9$ (wherein $R^9$ is hydrogen atom, alkyl, heteroalkyl, aryl, heteroaryl, arylalkyl or heteroarylalkyl), acyl, $COOR^{10}$ (wherein $R^{10}$ is alkyl, aryl or heteroaryl), carbamoyl, and $SO_2R^{11}$ (wherein $R^{11}$ is alkyl, heteroalkyl, aryl or heteroaryl). Also, the amino group may be a 5- or 6-memberd cyclic amino group, which ring may contain one or two additional heteroatoms selected from N, O and S. Further, the cyclic amino group may have at least one substituent selected from alkyl, heteroalkyl, aryl, heteroaryl, arylalkyl, heteroarylalkyl, oxo, halogen atom, hydroxy and alkoxy groups at a feasible position.

The acyl is a carbonyl group having hydrogen atom, alkyl, heteroalkyl, aryl, heteroaryl, alkenyl or alkynyl. Examples thereof include acetyl, propionyl, butyryl, acryloyl, benzoyl and the like. The acyl of $R^A$ and $R^B$ is preferably a carbonyl group having hydrogen atom, alkyl, heteroalkyl, aryl or heteroaryl.

The carbamoyl ($-CONH_2$) can be unsubstituted or substituted carbamoyl. The substituted carbamoyl includes that having one or two substituents selected from alkyl, heteroalkyl, aryl, heteroaryl, arylalkyl, heteroarylalkyl, alkoxy, arylalkoxy and hydroxy groups. Also, in the substituted carbamoyl group of $R^A$, the nitrogen atom in the carbamoyl group may be a member of 5- or 6-membered hetero ring. This 5- or 6-membered hetero ring may contain one or two additional heteroatoms selected from N, O and S. Also, the hetero ring may have at least one substituent selected from the group of alkyl, heteroalkyl, aryl, heteroaryl, arylalkyl, heteroarylalkyl, oxo, halogen atom, hydroxy and alkoxy groups at a feasible position.

The imino can be unsubstituted imino (=NH) or substituted imino (=$NR^9$). $R^9$ includes alkyl, heteroalkyl, aryl, heteroaryl, arylalkyl, heteroarylalkyl, $OR^{12}$ (wherein $R^{12}$ is hydrogen atom, alkyl, heteroalkyl, aryl, heteroaryl, arylalkyl or heteroarylalkyl), acyl, $COOR^{13}$ (wherein $R^{13}$ is alkyl, heteroalkyl, aryl, heteroaryl, arylalkyl or heteroarylalkyl), carbamoyl and amino.

Further, unless there is any problem, each substituent may be substituted by one or more substituents at a feasible position. Such a substituent includes alkyl, alkenyl, alkynyl, alkoxy, alkylamino, heteroalkyl, aryl, arylalkyl, aryloxy, arylamino, heteroaryl, heteroarylalkyl, heteroaryloxy, heteroarylamino, acyl, hydroxy, oxo, thioxo, carboxyl, alkoxycarbonyl, halogen atom, amino, nitro, mercapto, alkylthio and cyano. These substituents can be also combined.

| Compounding Example 1 Cream | |
|---|---|
| (1) Stearic acid | 5.0 weight % |
| (2) Stearyl alcohol | 4.0 |
| (3) Isopropyl myristate | 18.0 |
| (4) Glyceryl monostearate | 3.0 |
| (5) Propylene glycol | 10.0 |
| (6) Compound 1 | 0.001 |
| (7) Vitamin E acetate | 0.05 |
| (8) Potassium hydroxide | 0.2 |
| (9) Sodium hydrogensulfite | 0.01 |
| (10) Phenoxyethanol | 0.02 |
| (11) Perfume | q.s. |
| (12) Ion-exchange water | Balance |

(Preparing Method)

(5) and (8) were added and dissolved into (12), and then heated and maintained at 70° C. (a water phase). On the other hand, (1)–(4), (6), (7) and (9)–(11) were mixed together, melted with heating, and then maintained at 70° C. (a oil phase). The oil phase was added to the water phase slowly, and after completion of adding the mixture was kept at the temperature for a while. Then, the mixture was emulsified by a homomixer to be uniform, and then cooled to 30° C. while being mixed well, to give a cream.

| Compounding Example 2 Cream | |
|---|---|
| (1) Stearic acid | 2.0 weight % |
| (2) Stearyl alcohol | 7.0 |
| (3) Hydrogenated lanolin | 2.0 |
| (4) Squalane | 5.0 |
| (5) 2-Octyldodecyl alcohol | 6.0 |
| (6) POE(25)cetyl ether | 3.0 |
| (7) Glyceryl monostearate | 2.0 |
| (8) Propylene glycol | 5.0 |
| (9) Magnesium ascorbylphosphate | 0.1 |
| (10) Compound 2 | 0.001 |
| (11) Sodium hydrogensulfite | 0.03 |
| (12) Ethylparaben | 0.3 |
| (13) Perfume | q.s. |
| (14) Ion-exchange water | Balance |

(Preparing Method)

(8) and (9) were added to (14), and then heated and maintained at 70° C. (a water phase). On the other hand, (1)–(7) and (10)–(13) were mixed together, melted with heating, and then maintained at 70° C. (a oil phase). The oil phase was added to the water phase, and the mixture was pre-emulsified. Then, the mixture was emulsified by a homomixer to be uniform, and cooled to 30° C. while being mixed well, to give a cream.

| Compounding Example 3 Cream | |
|---|---|
| (1) Solid paraffin | 5.0 weight % |
| (2) Beeswax | 10.0 |
| (3) Vaseline | 15.0 |
| (4) Liquid paraffin | 41.0 |
| (5) Glyceryl monostearate | 2.0 |
| (6) POE(20)sorbitan monolaurate | 2.0 |
| (7) Soap powder | 0.1 |
| (8) Borax | 0.2 |
| (9) Soybean lysolecithin | 0.1 |
| (10) Compound 3 | 0.01 |
| (11) Sodium hydrogensulfite | 0.03 |
| (12) Ethylparaben | 0.3 |
| (13) Perfume | q.s. |
| (14) Ion-exchange water | Balance |

(Preparing Method)

(7), (8) and (9) were added to (14), and then heated and maintained at 70° C. (a water phase). On the other hand, (1)–(6) and (10)–(13) were mixed together, melted with heating, and then maintained at 70° C. (a oil phase). The oil phase was added to the water phase, and the mixture was pre-emulsified. Then, the mixture was emulsified by a homomixer to be uniform, and cooled to 30° C. while being mixed well, to give a cream.

| Compounding Example 4 Milky lotion | |
|---|---|
| (1) Stearic acid | 2.5 weight % |
| (2) Cetyl alcohol | 1.5 |
| (3) Vaseline | 5.0 |
| (4) Liquid paraffin | 10.0 |
| (5) POE(10)monooleate | 2.0 |
| (6) Polyethylene glycol 1500 | 3.0 |
| (7) Triethanolamine | 1.0 |
| (8) Carboxyvinyl polymer (Carbopol 941, B.F. Goodrich Corp.) | 0.05 |
| (9) Beech buds extract | 0.1 |
| (10) Compound 4 | 0.001 |
| (11) Sodium hydrogensulfite | 0.01 |
| (12) Ethylparaben | 0.3 |
| (13) Perfume | q.s. |
| (14) Ion-exchange water | Balance |

(Preparing Method)

(8) was dissolved in a small amount of (14) (Phase A). On the other hand, (6), (7) and (9) were added to the rest of (14), dissolved with heating, and then maintained at 70° C. (a water phase). (1)–(5) and (10)–(13) were mixed together, melted with heating, and then maintained at 70° C. (a oil phase). The oil phase was added to the water phase, and the mixture was pre-emulsified. Then, the mixture, with the Phase A added thereto, was emulsified by a homomixer to be uniform, and cooled to 30° C. while being mixed well, to give a milky lotion.

| Compounding Example 5 Milky lotion | |
|---|---|
| (1) Microcrystalline wax | 1.0 weight % |
| (2) Beeswax | 2.0 |
| (3) Lanolin | 20.0 |
| (4) Liquid paraffin | 10.0 |
| (5) Squalane | 5.0 |
| (6) Sorbitan sesquioleate | 4.0 |
| (7) POE(20)sorbitan monooleate | 1.0 |
| (8) Propylene glycol | 7.0 |
| (9) Gambir extract | 0.1 |
| (10) Compound 1 | 2.0 |
| (11) Sodium hydrogensulfite | 0.01 |
| (12) Ethylparaben | 0.3 |
| (13) Perfume | q.s. |
| (14) Ion-exchange water | Balance |

(Preparing Method)

(8) and (9) were added to (14), and then heated and maintained at 70° C. (a water phase). On the other hand, (1)–(7) and (10)–(13) were mixed together, melted with heating, and then maintained at 70° C. (a oil phase). The water phase was added to the oil phase slowly while being mixed. The mixture was emulsified by a homomixer to be uniform, and cooled to 30° C. while being mixed well, to give a milky lotion.

| Compounding Example 6 Gel | |
|---|---|
| (1) 95% Ethanol | 10.0 weight % |
| (2) Dipropylene glycol | 15.0 |
| (3) POE(50)oleyl ether | 2.0 |
| (4) Carboxyvinyl polymer (Carbopol 941, B. F. Goodrich Corp.) | 1.0 |
| (5) Sodium hydroxide | 0.15 |
| (6) L-Arginine | 0.1 |
| (7) Compound 2 | 1.0 |
| (8) Vitamin E acetate | 0.05 |
| (9) Sodium 2-hydroxy-4-methoxybenzophenone sulfonate | 0.05 |
| (10) Trisodium ethylenediamine tetraacetate 2-hydrate | 0.05 |
| (11) Methylparaben | 0.2 |
| (12) Perfume | q.s. |
| (13) Ion-exchange water | Balance |

(Preparing Method)

(4) was dissolved in (13) uniformly (a water phase). On the other hand, (3), (7) and (8) were dissolved in (1), and the mixture was added to the water phase. Then, (2) and (9)–(12) were added thereto, and the mixture was neutralized with (5) and (6), to give a gel.

| Compounding Example 7 Essence | |
|---|---|
| Phase A: | |
| 95% Ethanol | 10.0 weight % |
| POE(20)octyldodecanol | 1.0 |
| Pantothenyl ethyl ether | 0.1 |
| Compound 3 | 1.0 |
| Methylparaben | 0.15 |
| Phase B: | |
| Potassium hydroxide | 0.1 |

-continued

| Compounding Example 7 Essence | |
|---|---|
| Phase C: | |
| Glycerin | 5.0 |
| Dipropylene glycol | 10.0 |
| Sodium hydrogensulfite | 0.03 |
| Carboxyvinyl polymer (Carbopol 940, B.F. Goodrich Corp.) | 0.2 |
| Magnesium ascorbylphosphate | 0.1 |
| Soybean lysolecithin | 0.1 |
| Purified water | Balance |

(Preparing Method)
Phase A and Phase C each were dissolved uniformly. Phase C was added and solubilized into Phase A, and then Phase B added thereto. The mixture was filled up in a container, to give an essence.

| Compounding Example 8 Pack | |
|---|---|
| Phase A: | |
| Dipropylene glycol | 5.0 weight % |
| POE(60)hardened castor oil | 5.0 |
| Phase B: | |
| Compound 4 | 0.01 |
| Olive oil | 5.0 |
| Tocopherol acetate | 0.2 |
| Ethylparaben | 0.2 |
| Perfume | 0.2 |
| Phase C: | |
| Sodium hydrogensulfite | 0.03 |
| Polyvinyl alcohol (saponification degree 90, polymerization degree 2,000) | 13.0 |
| Ethanol | 7.0 |
| Soybean lysolecithin | 0.1 |
| Beech buds extract | 0.1 |
| Purified water | Balance |

(Preparing Method)
Phase A, Phase B and Phase C each were dissolved uniformly. Phase B was added and solubilized into Phase A, and then Phase C was added thereto. The mixture was filled up in a container, to give a pack.

| Compounding Example 9 Solid foundation | |
|---|---|
| (1) Talc | 43.0 weight % |
| (2) Kaolin | 15.0 |
| (3) Sericite | 10.0 |
| (4) Zinc oxide | 7.0 |
| (5) Titanium dioxide | 3.6 |
| (6) Yellow iron oxide | 2.9 |
| (7) Black iron oxide | 0.2 |
| (8) Squalane | 8.0 |
| (9) Isostearic acid | 4.0 |
| (10) POE sorbitan monooleate | 3.0 |
| (11) Isocetyl octanoate | 2.0 |
| (12) Vitamin E acetate | 0.05 |
| (13) Compound 1 | 1.0 |
| (14) Beech buds extract | 0.1 |
| (15) Antiseptics | q.s. |
| (16) Perfume | q.s. |

(Preparing Method)
Powder components of (1)–(7) were mixed by a blender thoroughly, and then oil components of (8)–(13) and components of (14)–(16) were added and well-kneaded therein. The mixture was filled up and formed in a container, to give a solid foundation.

| Compounding Example 10 Emulsion type foundation (Cream type) | |
|---|---|
| Powder part: | |
| Titanium dioxide | 10.3 weight % |
| Sericite | 5.4 |
| Kaolin | 3.0 |
| Yellow iron oxide | 0.8 |
| Red iron oxide | 0.3 |
| Black iron oxide | 0.2 |
| Oil phase: | |
| Decamethylcyclopentasiloxane | 11.0 |
| Liquid paraffin | 4.4 |
| POE dimethylpolysiloxane | 4.0 |
| Compound 2 | 1.0 |
| Octyl methoxycinnamate | 0.5 |
| Vitamin E acetate | 0.05 |
| Water phase: | |
| Purified water | 51.0 |
| 1,3-Butylene glycol | 4.5 |
| Sorbitan sesquioleate | 3.0 |
| Gambir extract | 0.1 |
| Antiseptics | q.s. |
| Perfume | q.s. |

(Preparing Method)
The water phase components except for perfume were stirred together with heating, and the powder part, which was mixed and grinded thoroughly, was added thereto. The mixture was treated by a homomixer, and then the oil phase, which was mixed with heating, was added thereto. After being treated by the homomixer, the mixture, with perfume added thereto while being stirred, was cooled to room temperature, to give an emulsion type foundation.

As explained foregoing, since the azabicyclo compound (I) of the present invention is effective as a matrix metalloproteases (MMPs) inhibitor, it can be incorporated into various pharmaceutical and cosmetic products. In particular, it can be applied to a skin external composition for the purpose of improving or preventing skin-aging, or to a composition for treating or preventing various diseases due to abnormal metabolism of tissue matrix such as arthritis, tissue ulcer formation, metastasis or infiltration of tumor and the like.

What is claimed is:
1. An azabicyclo compound or a salt thereof represented by the following formula (I):

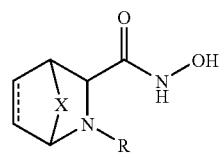

wherein R is hydrogen atom, alkyl, heteroalkyl, aryl, heteroaryl, arylalkyl, heteroarylalkyl, acyl, $COOR^1$, carbamoyl or $SO_2R^2$;

wherein R¹ and R² each are alkyl, heteroalkyl, aryl, heteroaryl, arylalkyl or heteroarylalkyl;

X is methylene, ethylene or propylene; and

----- is a single bond or a double bond.

2. The azabicyclo compound or a salt thereof according to claim 1, wherein R is $SO_2R^2$.

3. The azabicyclo compound or a salt thereof according to claim 2, wherein $R^2$ is aryl.

4. The azabicyclo compound or a salt thereof according to claim 1, wherein X is methylene.

5. The azabicyclo compound or a pharmacologically acceptable salt thereof according to claim 1, wherein said azabicyclo compound or a pharmacologically acceptable salt thereof is a matrix metalloprotease inhibitor.

6. The azabicyclo compound or a pharmacologically acceptable salt thereof according to claim 1, wherein said azabicyclo compound or a pharmacologically acceptable salt thereof is included in a cosmetic composition.

7. The azabicyclo compound or a pharmacologically acceptable salt thereof according to claim 1, wherein said azabicyclo compound or a pharmacologically acceptable salt thereof is included in a pharmaceutical composition.

8. The azabicyclo compound or a pharmacologically acceptable salt thereof according to claim 1, wherein said azabicyclo compound or a pharmacologically acceptable salt thereof is included in a skin external composition.

9. A method for inhibiting metalloprotease matrix activity, which comprises administering an effective amount of the azabicyclo compound or a pharmacologically acceptable salt thereof according to claim 1 to a mammal.

10. The method according to claim 9, wherein said metalloprotease matrix activity is related to skin-aging.

11. The method according to claim 9, wherein said metalloprotease is a gelatinase group matrix metalloprotease-9 (MMP-9).

12. The method according to claim 11, wherein said gelatinase group MMP-9 is in skin of said mammal.

* * * * *